(12) United States Patent
Deronzier et al.

(10) Patent No.: US 9,203,080 B2
(45) Date of Patent: Dec. 1, 2015

(54) RECHARGEABLE METAL OR METAL-ION CELL

(75) Inventors: Alain Deronzier, Meylan (FR); Thibault Godet-Bar, Saint-Martin-d'Heres (FR); Jean-Claude Lepretre, Voreppe (FR); Jean-Yves Sanchez, Saint Ismier (FR)

(73) Assignees: Solvay SA, Brussels (BE); Universite Joseph Fourier, Grenoble (FR)

( * ) Notice: Subject to any disclaimer, the term of this patent is extended or adjusted under 35 U.S.C. 154(b) by 201 days.

(21) Appl. No.: 13/885,049

(22) PCT Filed: Nov. 16, 2011

(86) PCT No.: PCT/EP2011/070272
§ 371 (c)(1),
(2), (4) Date: May 13, 2013

(87) PCT Pub. No.: WO2012/066048
PCT Pub. Date: May 24, 2012

(65) Prior Publication Data
US 2013/0230771 A1 Sep. 5, 2013

(30) Foreign Application Priority Data

Nov. 16, 2010 (EP) ..................................... 10306259

(51) Int. Cl.
*H01M 4/137* (2010.01)
*C07D 279/20* (2006.01)
(Continued)

(52) U.S. Cl.
CPC ............. *H01M 4/137* (2013.01); *C07D 279/20* (2013.01); *C07D 279/22* (2013.01);
(Continued)

(58) Field of Classification Search
None
See application file for complete search history.

(56) References Cited

U.S. PATENT DOCUMENTS 3,925,369 A  12/1975  Vincent et al.
4,472,487 A   9/1984  Maxfield et al.
(Continued)

FOREIGN PATENT DOCUMENTS

EP  0205913 A2  12/1986
EP  1950207 A1   7/2008
(Continued)

OTHER PUBLICATIONS

Koji Nishio, et al—"Characteristics of a lithium secondary battery using chemically-synthesized conductive polymers", 1991, Journal of Power Sources, vol. 34, Issue No. 2, pp. 153-160; 8 pgs.
(Continued)

*Primary Examiner* — Patrick Ryan
*Assistant Examiner* — Christopher Domone

(57) ABSTRACT

A rechargeable metal ion cell comprising: an anode comprising at least one metal; a charge-carrying electrolyte comprising a charge carrying medium and at least one metal salt; and an organic polymer cathode, wherein such cathode comprises at least one N-substituted polyphenothiazine polymer [polymer (P)], such polymer (P) comprising at least one N-substituted phenothiazine recurring unit of formula:

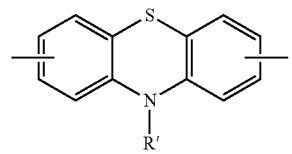

wherein R' is an electron-withdrawing group comprising at least one heteroatom selected from the group consisting of O, S, P, and N.

19 Claims, 3 Drawing Sheets

(51) Int. Cl.
| | |
|---|---|
| *C07D 279/22* | (2006.01) |
| *C07D 279/30* | (2006.01) |
| *H01M 4/60* | (2006.01) |
| *H01M 10/052* | (2010.01) |
| *H01M 10/054* | (2010.01) |
| *H01M 4/02* | (2006.01) |

(52) U.S. Cl.
CPC .............. *C07D 279/30* (2013.01); *H01M 4/60* (2013.01); *H01M 4/608* (2013.01); *H01M 10/052* (2013.01); *H01M 10/054* (2013.01); *H01M 2004/028* (2013.01); *Y02E 60/122* (2013.01)

(56) References Cited

U.S. PATENT DOCUMENTS

| | | | |
|---|---|---|---|
| 5,142,045 | A | 8/1992 | Zand et al. |
| 5,401,815 | A * | 3/1995 | Shimizu et al. ................. 526/62 |
| 6,203,944 | B1 | 3/2001 | Turner et al. |
| 2002/0028803 | A1 | 3/2002 | Bebbington et al. |
| 2004/0135131 | A1 | 7/2004 | Treacher et al. |
| 2007/0238858 | A1 | 10/2007 | Li et al. |
| 2009/0075161 | A1 * | 3/2009 | Ando et al. ..................... 429/94 |

FOREIGN PATENT DOCUMENTS

| | | | |
|---|---|---|---|
| JP | 62-232855 A | | 10/1987 |
| JP | 62-232856 A | | 10/1987 |
| JP | 62232856 | * | 10/1987 |
| WO | WO 8302368 A1 | | 7/1983 |
| WO | WO 0003444 A1 | | 1/2000 |
| WO | WO 0240460 A1 | | 5/2002 |
| WO | WO 2006124738 A1 | | 11/2006 |

OTHER PUBLICATIONS

Ji-Soung Kang, et al—"Synthesis and Properties of Poly(10-Octylphenothiazine-CO-2',3',6',7'-Tertrakis-Octyloxy-9-Spirobifluorene) for OLEDs", 2007, Molecular Crystals and Liquid Crystals, vol. 462, Issue No. 1, Copyright Taylor & Francis Group, LLC, pp. 267-276 [DOI:10.1080/15421400601013429]; 10 pgs.

Benrabah, D., et al—"Cationic conductivity in poly(oxyethylene oxide) networks", 1995, Journal of Power Sources, vol. 54, Issue No. 2, [DOI: 10.1016/0378-7753(94)02124-L], Elsevier Science SA; pp. 456-460; 5 pgs.

Pavlishchuk, V.V., et al—"Conversion constants for redox potentials measured versus different reference electrodes in acetonitrile solutions at 25 °C", 2000, Inorganica Chimica Acta, vol. 298, [DOI:10.1016/S0020-1693(99)00407-7], Elsevier Science SA, pp. 97-102; 6 pgs.

Darvesh, Sultan, et al—"Selective reversible inhibition of human butyrylcholinesterase by aryl amide derivatives of phenothiazine", 2007, Bioorganic & Medicinal Chemistry (ISSN 0968-0896), vol. 15, Issue No. 19, [DOI: 10.1016/j.bmc.2007.06.060], Elsevier Ltd., pp. 6367-6378; 12 pgs.

Veld, M.—"Use of PQT12 as a new material in organic solar cells—Graduation report of Martijn Veld", Jun. 2005, Molecular Materials and Nanosystems, Laboratory of Macromolecular and Organic Chemistry, Eindhoven University of Technology; pp. 1-52; 57 pgs.

Han, Y.S., et al—"Synthesis of Conjugated Copolymers Containing Phenothiazinylene Vinylene Moieties and Their Electrooptic Properties", 2003, Journal of Polymer Science Part A Polymer Chemistry, vol. 41, Issue No. 16, DOI:10.1002/pola.10793; Wiley Periodicals, Inc., pp. 2502-2511; 10 pgs.

Darvesh, S., et al—"Carbamates with Differential Mechanism of Inhibition Toward Acetylcholinesterase and Butyrylcholinesterase", 2008, Journal of Medicinal Chemistry, vol. 51, Issue No. 14, DOI:10.1021/jm8002075, pp. 4200-4212; 13 pgs.

Sailer, M., et al—"Synthesis and Electronic Properties of Monodisperse Oligophenothiazines", 2008, Chemistry-A European Journal, vol. 14, Issue No. 8, DOI:10.1002/chem.200701341, Wiley Interscience, Wiley-VCH Verlag GmbH & Co KGaA, Weinheim pp. 2602-2614; 13 pgs.

Marzocchi, E., et al—"Chemiluminescent detection systems of horseradish peroxidase employing nucleophilic acylation catalysts", 2008, Analytical Biochemistry, vol. 377, Issue No. 2, DOI:10.1016/j.ab.2008.03.020, pp. 189-194; 6 pgs.

Tsami, A., et al—"Alternating Fluorene-di(thiophene)quinoxaline Copolymers via Microwave-Supported Suzuki Cross-Coupling Reactions", 2008, Journal of Polymer Science Part A: Polymer Chemistry, vol. 46, Issue No. 23, DOI:10.1002/pola.23081,Wiley Periodicals, Inc., pp. 7794-7808; 15 pgs.

Melucci, M., et al—"Solvent-Free, Microwave-Assisted Synthesis of Thiophene Oligomers via Suzuki Coupling", 2002, The Journal of Organic Chemistry, vol. 67, Issue No. 25, DOI:10.1021/jo026269d, Copyright—American Chemical Society pp. 8877-8884; 8 pgs.

Britze, A., et al—"Synthesis of PPP-b-PS block copolymers using a combination of Suzuki-polycondensation and nitroxide-mediated radical polymerization", Sep. 17, 2010, Polymer, vol. 51, Issue No. 29, DOI:10.1016/j.polymer.2010.09.022, Elsevier Ltd., pp. 5294-5303; 10 pgs.

Rabindranath, A.R., et al—"Red Emitting N-Functionalized Poly(1,4-diketo-3,6-diphenylpyrrolo[3,4-c]pyrrole) (Poly-DPP): A Deeply Colored Polymer with Unusually Large Stokes Shift", 2006, Macromolecules, vol. 39, Issue No. 24, DOI:10.1021/ma061024e, pp. 8250-8256; 7 pgs.

Melucci, M., et al—"Solution-Phase Microwave-Assisted Synthesis of Unsubstituted and Modified α-Quinque- and Sexithiophenes", 2004, Journal of Organic Chemistry, vol. 69, Issue No. 14, DOI:10.1021/jo035723q, pp. 4821-4828; 8 pgs.

Yamamoto, T., et al—"Preparation of π-Conjugated Poly(thiophene-2,5-diyl), Poly(p-phenylene), and Related Polymers Using Zerovalent Nickel Complexes. Linear Structure and Properties of the π-Conjugated Polymers", 1992, Macromolecules, vol. 25, Issue No. 4, DOI:10.1021/ma00030a003, pp. 1214-1223; 10 pgs.

Yamamoto, T., et al—"A Novel Type of Polycondensation Utilizing Transition Metal-Catalyzed C-C Coupling. I. Preparation of Thermostable Polyphenylene Type Polymers", Jul. 1978, Bulletin of the Chemical Society of Japan, vol. 51, Issue No. 7, DOI:10.1246/bcsj.51.2091, pp. 2091-2097; 7 pgs.

Lafferty, J.J., et al—"The Synthesis of Phenothiazines. VII.1 Methyl- and Arylsulfonylation of Phenothiazine and its 10-Substituted Derivatives", Apr. 1962, The Journal of Organic Chemistry, vol. 27, Issue No. 4, DOI:10.1021/jo01051a052; pp. 1346-1351; 6 pgs.

Piggott, A.M., et al—"Hydrolysis rates of alkyl and aryl sulfinamides: evidence of general acid catalysis", 2007, Tetrahedron Letters, vol. 48, Issue No. 42, DOI:10.1016/j.tetlet.2007.08.081, Elsevier Ltd., pp. 7452-7455; 4 pgs.

Turhanen, P.A., et al—"First synthesis of etidronate partial amides starting from PCl$_3$ ", 2003, Organic and Biomolecular Chemistry, vol. 1, DOI:10.1039/B305979K, The Royal Society of Chemistry, pp. 3223-3226; 4 pgs.

* cited by examiner

RECHARGEABLE METAL OR METAL-ION CELL

CROSS REFERENCE TO RELATED APPLICATIONS

This application is a U.S. national stage entry under 35 U.S.C. §371 of International Application No. PCT/EP2011/070272 filed Nov. 16, 2011, which claims priority to European patent application No. 10306259.2 filed Nov. 16, 2010, the whole content of this application being incorporated herein by reference for all purposes.

TECHNICAL FIELD

The invention pertains to a cathode material for a rechargeable metal or metal-ion cell, including alkaline or alkaline-earth secondary batteries, used in, for example, a portable thin type electronic appliance or an electric vehicle. More particularly, the invention pertains to a cathode material for a lithium secondary battery, generally used as a power source requiring a high energy density. The invention further pertains to rechargeable metal or metal-ion cell (e.g. alkaline or alkaline-earth secondary batteries such as lithium batteries) comprising organic polymer cathodes.

BACKGROUND ART

When properly designed and constructed, rechargeable alkaline or alkaline-earth batteries, in particular lithium cells, can exhibit excellent charge-discharge cycle life, little or no memory effect, and high specific and volumetric energy.

In conventional lithium secondary batteries, particles of inorganic metal oxide such as lithium cobaltate ($LiCoO_2$) or lithium manganese oxide ($LiMnO_2$), generally mixed with conductive carbon black filler, are bound by a redox-inactive binder such as polyvinylidene fluoride and molded for being used as positive (cathode) electrode.

In recent years, secondary batteries having increased high energy density have come to be required, and organic materials have attracted attention as positive electrode materials capable of achieving such results.

Since conjugated electrically conductive polymers have been used as electrode materials for secondary batteries, much effort has been directed towards the development of this type of batteries. Actually, polymer batteries, i.e. batteries wherein an organic polymer is used as electrode, are expected to have many advantages, such as lighter weight, higher voltage, multiple shape capabilities, and a pollution-free construction, owing to the nature of the polymers.

Nevertheless, these polymer electrodes still have several drawbacks. In particular, electroactive polymers such as polypyrroles and polythiophenes generally possess unsatisfactory durability, poor cyclability and low oxidation potential values.

A system endowed with best current performances is based on the use of TEMPO (2,2,6,6-tetramethylpiperidine-1-oxyl) moieties as side chain of polymeric backbones. Main drawback of these systems are their limited oxidation potential, their slow kinetic of electron transfer and their low capacities, partly related to the need of incorporating in the polymer electrode substantial amounts of carbon black (generally about 50% of the overall electrode material) for ensuring suitable electronic conductivities.

Within these approaches, polymers comprising phenothiazine moieties have been considered as electrode materials.

In particular, WO 83/02368 (CHERON RESEARCH COMPANY) Jul. 7, 1983 discloses secondary batteries incorporating at least one electroactive organic polymer electrode, wherein said electroactive organic polymer is capable of undergoing a reversible oxidation or a reversible reduction to a charged conductive state, in which it exhibits a considerable stability. Among polymers which are reversibly oxidizable (p-type polymers) and which are thus especially well suited for use as cathodes, mention is made of certain fused 6,6,6-membered ring system polymers, among which those comprising diradicals of N-alkylphenothiazine are listed.

Properties of charge/discharge characteristics of various conductive polymers in lithium secondary battery assemblies are disclosed in NISHIO, Koji, et al. Characteristics of a lithium secondary battery using chemically-synthesized electrical conductive polymers. *Journal of Power Sources*. 1991, vol. 34, p. 153-160. In this investigation, a polyphenothiazine polymer of formula

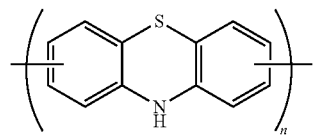

was used as cathode in a Li/polymer cell; nevertheless, cell voltage was found to reach 5.0 V immediately after charging started, failing thus to provide stable charge/discharge curves.

It is also known the use of phenothiazine compounds as redox shuttles in conventional Li batteries for protecting electrodes against surcharge.

Thus, WO 2006/124738 (3M INNOVATIVE PROPERTIES) Nov. 23, 2006 discloses lithium-ion cells comprising, inter alia, electrolyte having dissolved therein N-substituted or C-substituted phenothiazine compounds serving as cyclable redox shuttle for protecting cell against overcharge.

Nevertheless, there is currently a shortfall in the art for rechargeable lithium-ion cells having improved cyclability, high capacity and high voltage outputs in combination with lightweight and environmental friendliness.

SUMMARY OF THE INVENTION

It is thus an object of the present invention a rechargeable metal or metal-ion cell comprising:
- an anode comprising at least one metal;
- a charge-carrying electrolyte comprising a charge carrying medium and at least one metal salt;
- an organic polymer cathode, wherein said cathode comprises at least one N-substituted polyphenothiazine polymer [polymer (P)], said polymer comprising at least one N-substituted phenothiazine recurring unit of formula:

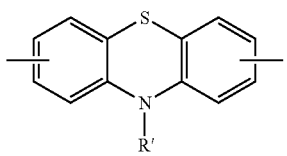

wherein R' is an electron-withdrawing group comprising at least one heteroatom selected from O, S, P and N.

Certain N-substituted phenothiazine monomers and polymers comprising recurring units derived from the same, which are particularly suitable to the purposes of the present invention, are another object of the present invention.

Figure 1:
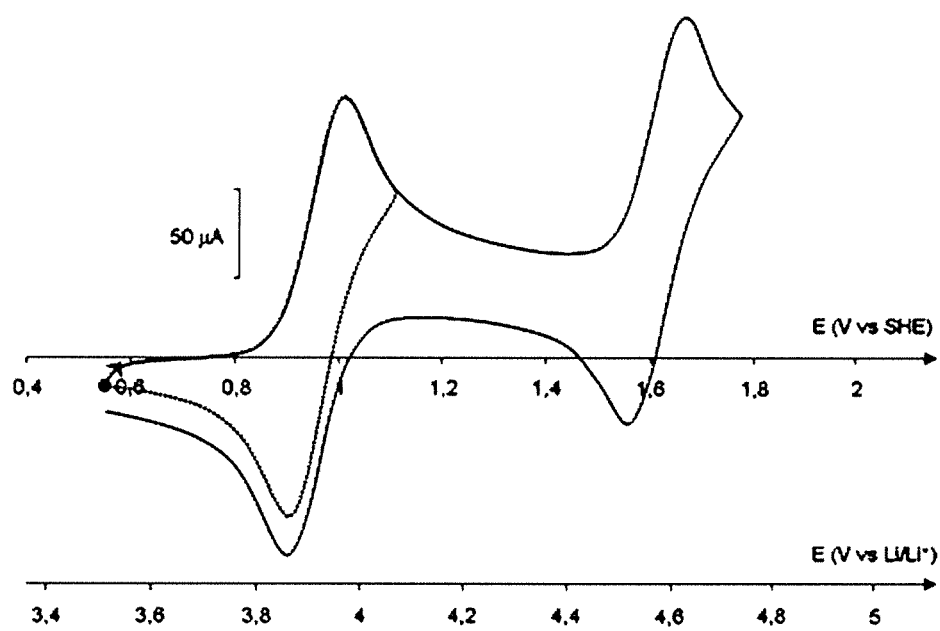
FIGS. 1 to 7 depict cyclic voltammetry traces recorded for various phenothiazine-based compounds in a $CH_3CN$+tetrabutyl ammonium perchlorate (TBAP) 0.1 M solution on a platinum electrode.

The phenothiazine-based compound a cyclic voltammetry trace of which is depicted in FIG. 1 is 10H-methylphenothiazine (hereinafter, compound II).

Figure 2:
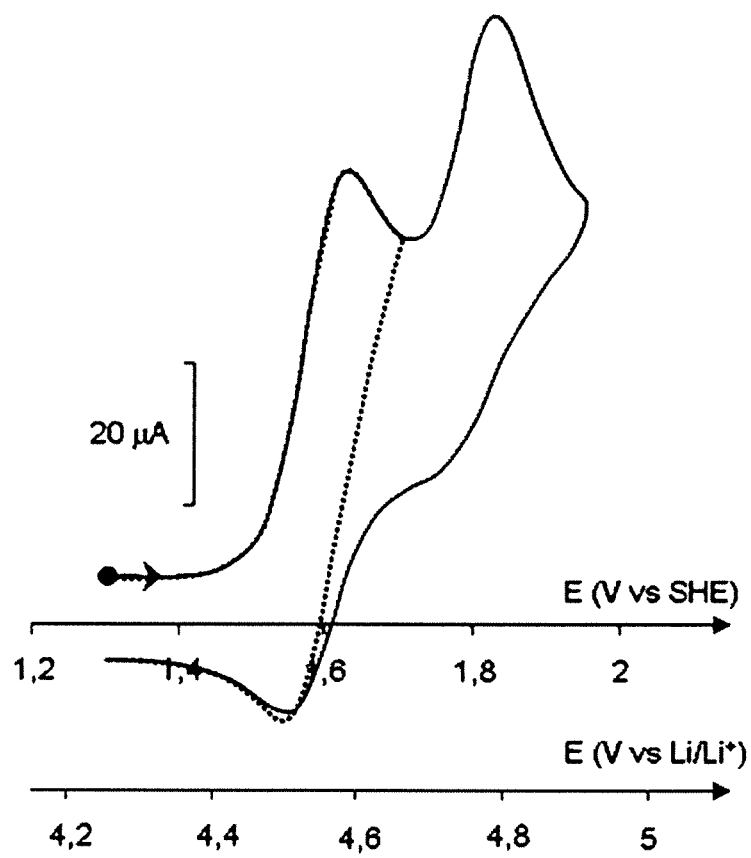

The compound a cyclic voltammetry trace of which is depicted in FIG. 2 is 10H-[1,1,1,2-tetrafluoro-3-oxopropane-2-lithium sulfonate]-phenothiazine (hereinafter, compound XI).

Figure 3:
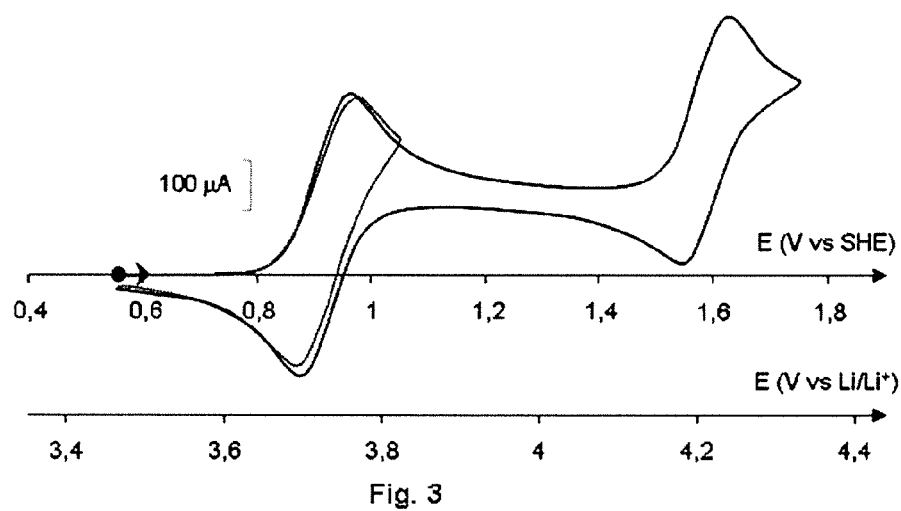

The compound a cyclic voltammetry trace of which is depicted in FIG. 3 is 10H-propylphenothiazine (hereinafter, compound VI).

Figure 4:
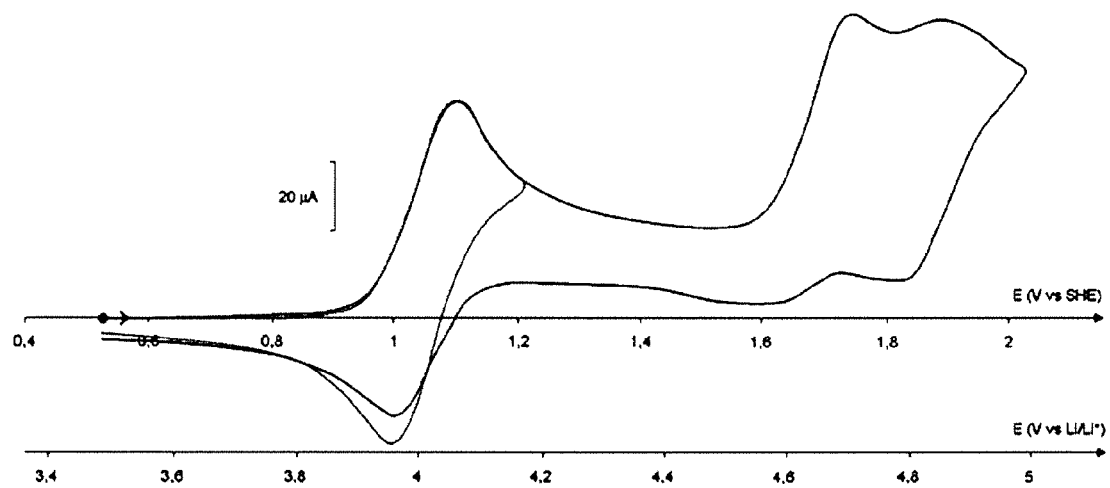

The compound a cyclic voltammetry trace of which is depicted in FIG. 4 is 3,3'-dibromo-10H-propylphenothiazine (hereinafter, compound VII).

Figure 5:
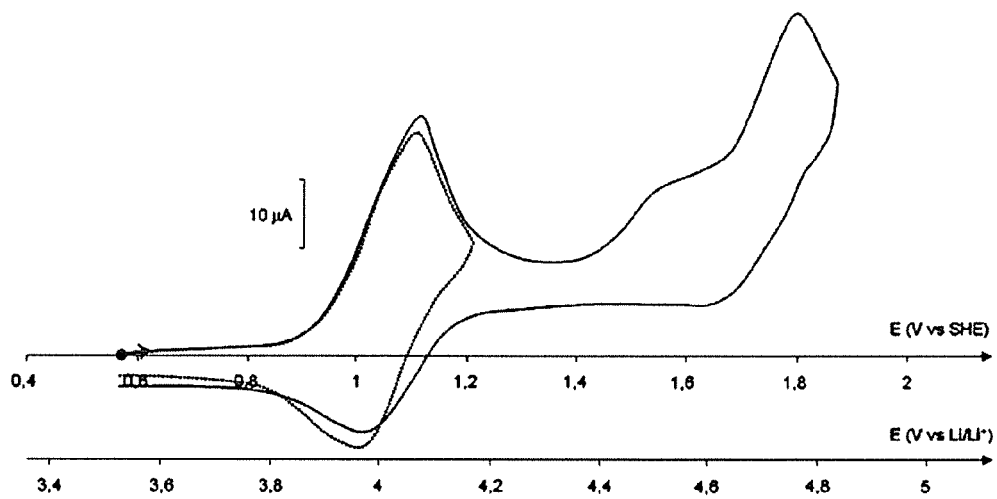

The compound a cyclic voltammetry trace of which is depicted in FIG. 5 is 3,3'-dibromo-10H-(lithium propanesulfonate)-phenothiazine (hereinafter, compound XIII).

Figure 6:
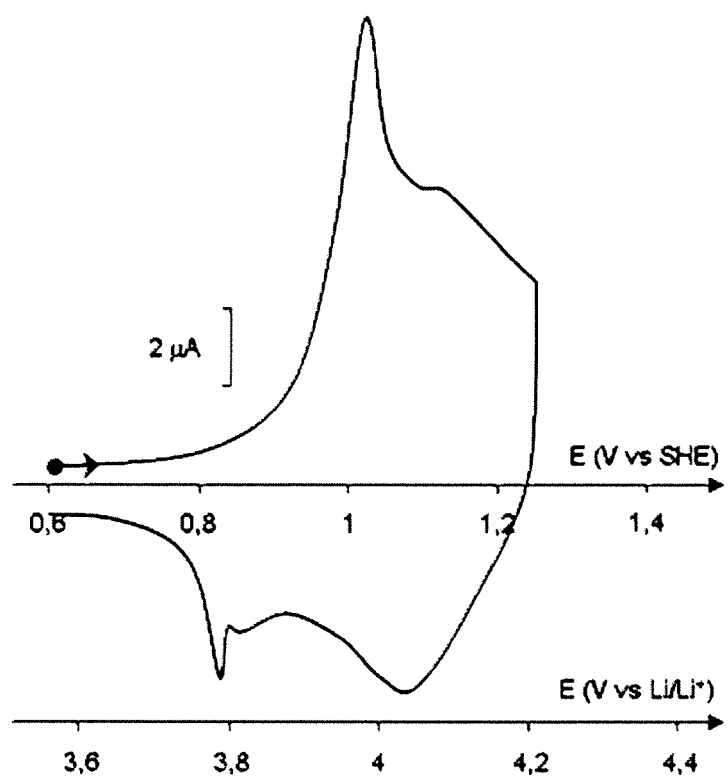

The compound a cyclic voltammetry trace of which is depicted in FIG. 6 is a polymer [hereinafter, Poly($II_c$)] prepared from 3,3'-dibromo-10H-methylphenothiazine [hereinafter, compound III], the polymer being in the form of a film casted from a $CH_2Cl_2$ solution.

Figure 7:
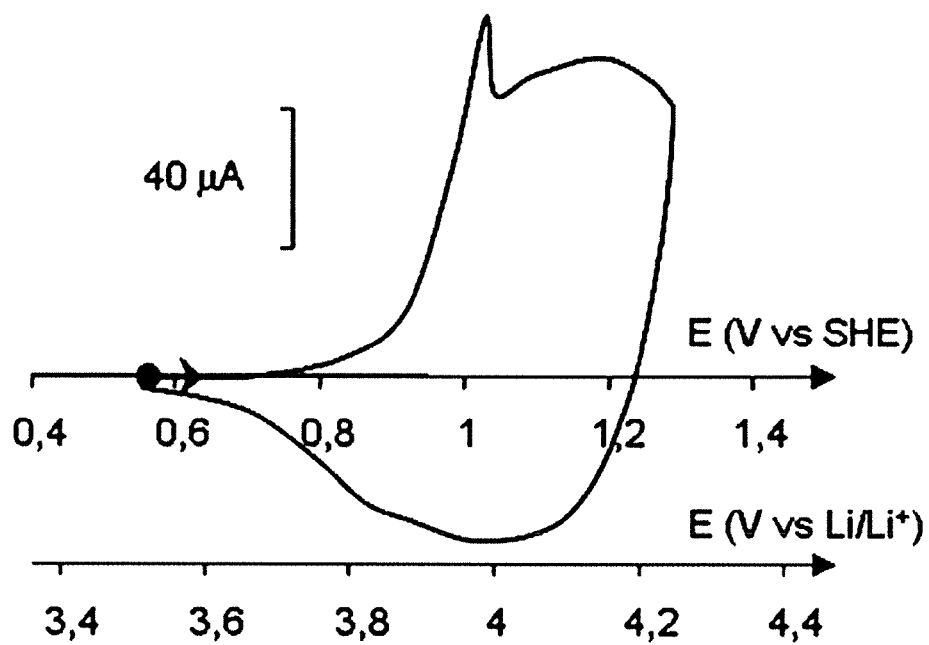

The compound the cyclic voltammetry trace of which is depicted in FIG. 7 is a polymer [hereinafter, Poly($VIII_b$)] prepared from 3,3'-dibromo-10H-heptylphenothiazine [hereinafter, compound IX], the polymer being in the form of a film casted from a $CH_2Cl_2$ solution.

DETAILED DESCRIPTION OF THE INVENTION

The Applicant has found that by appropriate selection of the electron-withdrawing group onto the phenothiazine ring, it is advantageously possible to obtain polymers having outstanding filmability and tixotropic properties, enabling manufacture of cathode having intrinsic electric conductivity and further possessing oxidation potentials higher than 4 V vs Li/Li$^+$ (corresponding typically at about 1 V on a SHE scale), which are comparable to those achievable with inorganic cathodes (e.g. with lithium calcogenides or other mixed oxides). Further, the batteries of the invention have been found to provide outstanding cyclability and high electron and ion conductivity so that connection between the cathode material and the collectors are significantly improved even with reduced amounts of conductive additives (typically carbon black).

Due to the easy processability and tixotropic properties of above mentioned N-substituted phenothiazine polymers, batteries as above described can be easily manufactured by means of typical processing technologies applicable to soluble polymers, with substantially no use of additional binders.

The rechargeable metal ion cell of the invention can be notably a secondary transition metal battery, e.g. a Vanadium redox battery; an alkaline or alkaline-earth secondary battery, like lithium, sodium, magnesium, calcium battery, with lithium batteries being preferred.

In the N-substituted phenothiazine polymer [polymer (P)] of the invention the R' group typically forms with the nitrogen atom of the phenothiazine ring at least one electron-withdrawing group selected from the group consisting of urethane group; urea group; thiourethane group; amide group; sulphonamide groups; sulphinamide group; hydrazine group; phosphonamide group, phosphinimide group, phosphamide group.

Non limitative examples of N-substituted phenothiazine recurring units of the polymer (P) are those complying with anyone of formulae herein below:

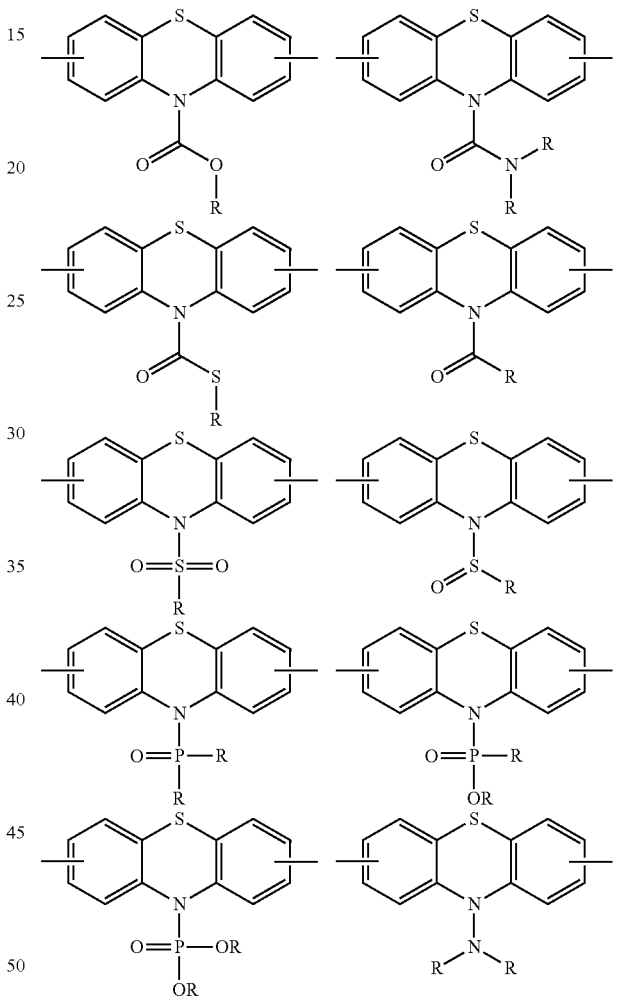

wherein each of R, equal or different from each other and at each occurrence are selected from H or from a hydrocarbon group, possibly fluorinated, and optionally comprising one or more ionisable group.

According to an embodiment of the invention, the N-substituted phenothiazine recurring unit as above described of polymer (P) additionally comprises at least one ionisable group. These ionisable groups, intrinsically providing to the polymer (P) ionic conductivity, can enhance performances of the polymer (P) in the rechargeable metal or metal-ion cell of the invention, thanks to their ability to exchange metal cations, e.g. Lithium cations.

Among ionisable groups, mention can be notably made of carboxylate groups, sulphonate groups, sulphonylimide groups, phosphonate groups, with sulphonate and sulphonylimide groups being preferred.

Said groups might be bound to the phenyl moieties of the N-substituted phenothiazine or might be comprised in the electron-withdrawing group R', as above described, this last embodiment being preferred.

According to said embodiment, the ionisable group can be a substituent of anyone of group R of above depicted representative embodiments of the N-substituted phenothiazine recurring units of polymer (P).

Polymers (P) comprising recurring units selected from the group consisting of:

(I) urethane-containing phenothiazine recurring units of formula:

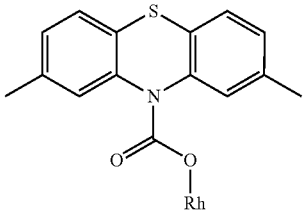

wherein Rh is a $C_1$-$C_{24}$ hydrocarbon group, possibly fluorinated, optionally comprising one or more heteroatoms comprised in an additional functional group;

(II) amide-containing phenothiazine recurring units of formula:

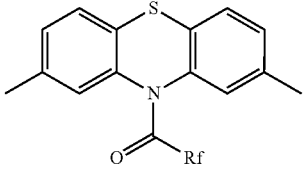

wherein Rf is a $C_1$-$C_{24}$ hydrocarbon group, preferably fluorinated optionally comprising one or more heteroatoms comprised in an additional functional group.

Polymer (P) of the invention can notably comprise, in addition to recurring units containing the N-substituted phenothiazine group as above defined, additional recurring units different from the above.

For instance, the polymer (P) can be a copolymer comprising e.g. recurring units of a N-substituted phenothiazine monomer and recurring units derived from another monomer, like notably, an aromatic monomer, e.g. a heteroaromatic monomer, like a phenothiazine monomer different from the above.

These comonomers can be notably introduced with the aim of improving solubility and/or processability of the resulting polymer (P).

These comonomers might comprise fused 6,6,6-membered ring systems, fused 5,6-membered ring systems, 5,6,5-membered ring systems or monocyclic heterocyclic ring systems.

Suitable fused 6,6,6-membered ring system comonomers are those comprising diradicals of thianthrenes, phenoxathiins, phenoxazine, N-alkylphenothiazine dihydrophenazine, dialkyldihydrophenazine, dibenzodioxin, their substituted derivatives and mixtures thereof. The diradicals can be connected through the outer carbocyclic rings or a carbocyclic ring and a nitrogen in the central ring.

Suitable fused 5,6-membered ring system comonomers are those comprising diradicals of benzoxazole, benzothiazole, benzoselenazole, N-alkyl-substituted benzimidazole, their substituted derivatives, and the like.

Suitable 5,6,5-membered ring system comonomers are those comprising diradicals of of I,7-dialkyl-benzo[1,2-d:4,5-d']diimidazoles, such as 1,7-dimethyl-benzo[1,2,-d:4,5-d'] diimidazole; benzo[1,2-d:5,4-d']bisthiazole; benzo[1,2-d:4,5-d']bisthiazole; benzo[1,2-d:4,5-d']bis-selenazole; benzo[I,2-d:4,5-d']bisselenazole; benzo[I,2-d:4,5-d']bistellurazole; selenazolo[5,4-f]benzothiazole; 1,8-dialkyl-benzo[1,2-d:3,4-d']diimidazoles, such as 1,8-dialkyl-benzo[1,2-d:3,4-d']diimidazole; benzo[1,2-d:5,4-d']bisoxazole; benzo[1,2-d:4,5-d']bisoxazole; benzo[I,2-d:3,4-d']bisoxazole; benzo[1,2-:3,4-d']bisthiazole; their substituted derivatives; and mixtures thereof.

Suitable monocyclic heterocyclic ring system comonomers are those comprising diradicals of triazoles, heterodiazoles such as thiadiazole, oxadiazole, and the like, and heteroazoles such as oxazole and thiazole, all said monocyclic heterocyclic systems incorporating 1,4-phenylene as a connecting unit.

Suitable examples of single-nitrogen, fused-ring system comonomers are those comprising diradicals of quinoline and isoquinoline. Suitable examples of two-nitrogen, fused-ring system comonomers are those comprising diradicals of cinnoline; quinazoline; quinoxaline; 2-phenylquinoxaline; phthalazine; 1,5-naphthyridine; 1,6-naphthyridine; 1,7-naphthyridine; 1,8-naphthyridine; 2,6-naphthyridine; copyrine; and the like. Suitable examples of three-nitrogen, fused-ring system comonomers are those comprising diradicals of 1,2,4-benzotriazine; pyrido[3,2-d]pyrimidine; pyrido[4,3-d]pyrimidine; pyrido[3,4-d]pyrimidine; pyrido[2,3-d]pyrimidine; pyrido[2,3-b]pyrazine; pyrido[3,4-b]pyrazine; pyrido(2,3-d]pyridazine; pyrido[3,4-d]pyridazine; and the like. Suitable examples of four-nitrogen, fused-ring system comonomers are those comprising diradicals of pyridazino[4,5-c]pyridazine; pyrimido[5,4-d]pyrimidine; pteridine; pyrimido[4,5-d]pyridazine; pyrimido[4,5-d]pyrimidine; pyrazino[2,3-b]pyrazine; pyrazino[2,3-d]pyridazine; pyridazino[4,5-d]yridazine; pyrimido[4,5-c]pyridazine; pyrazino[2,3-c]pyridazine; pyrido[3,2-d]-as-triazine; pyrido[2,3-e]-as-triazine; and the like. Suitable examples of five-nitrogen, fused ring system comonomers are those comprising diradicals of pyrimido[4,5-e]-as-triazine; pyrimido[5,4-d]-as-triazine; and the like. Suitable examples of six-nitrogen, fused-ring systems are any of the diradicals of as-triazino[6,5-d]-as-triazine; and the like.

Nevertheless, embodiments wherein polymer (P) only comprise recurring units derived from a N-substituted phenothiazine monomer are preferred.

Polymers (P) which have been found particularly suitable to be used in the rechargeable metal-ion cell are those comprising recurring units of formula (I-A) and/or (II-A) herein below:

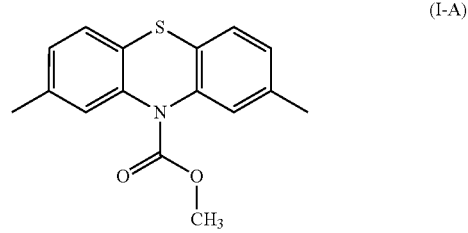

(I-A)

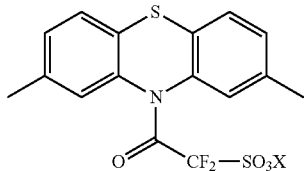

(II-A)

X in formula (II-A) being a metal, preferably an alkaline metal, more preferably Li.

The molecular weight distribution MWD of polymer (P) can be determined by gel permeation chromatography (GPC) using THF as solvent and polystyrene calibration standards. Following equipments, materials and operating conditions can notably be used:

- pump: WATERS 515 HPLC;
- columns: coupling 06: WATERS: Styragel® HR4+Styragel® HR 3, thermostatized at 35° C.;
- refractometry detector: SOPARES RI2000 at 40° C.;
- light-diffusion detector: WYATT DAWN EOS at 690 nm (18 angles);
- solvent: ACROS THF for analysis ACS with 0.025% BHT;
- solvent filter: on-line 0.2 μm propylene filter;
- solvent flow: 1 ml/min;
- injected volume: 50 μl;
- sample concentration: 1 wt. %;
- sample pre-filtering: single use 0.45 μm PTFE pre-filter;
- acquisition and handling: ASTRA software, model 4.90.07.

As well known to the skilled person, the weight average molecular weight, the number average molecular weight and, directly related thereto, the number average degree of polymerization DPn (i.e. the number average of monomer repeat units, hereinafter named "patterns") can be easily obtained from the so-determined MWD.

$$DP_n = M_n/MM$$

wherein $M_n$ is the number average molecular weight of polymer (P) and MM is the molecular weight of a single monomer repeat unit of polymer (P).

The number average degree of polymerization of polymer (P) $DP_n$ is not particularly limited. Usually, $DP_n$ ranges from 2 to 200, but polymers (P) wherein $DP_n$ exceeds 200, possibly up to 500, up to 1,000, up to 2,000, up to 5,000 or even up to 10,000, can also be useful.

$DP_n$ is preferably of at least 3, more preferably of at least 5 and still more preferably of at least 8; it may be of at least 10. On the other hand, it is preferably of at most 100, more preferably at most 50, still more preferably of at most 20; it may be of at most 16 or at most 13.

Besides, the weight average molecular weight of polymer (P) $M_w$ ranges in general from about 500 to about 100,000, but polymers (P) wherein $M_w$ exceeds 100,000 (e.g. polymers (P) having a $M_w$ up to about 10,000,000) can also be useful.

Good results were notably obtained with polymers (P) having a $M_w$ from 1,000 to 15,000. Excellent results were notably obtained with polymers (P) having a $M_w$ from 1,500 to 7,500, in particular from 2,000 to 6,000.

Polymers (P) as above detailed can be manufactured by techniques well-known to those skilled in the art.

Well known techniques for the coupling of aromatic compounds having halogen (typically bromine or iodine) group, borane groups or other labile groups can be effectively used for manufacturing polymer (P) from suitable N-substituted phenothiazine monomer derivatives.

In particular Suzuki reaction, involving the reaction of diboron derivatives and transition metal catalysts, typically Pd-based catalyst, and Yamamoto reaction, involving halogenated dibrominated derivatives, and transition metal catalysts, preferably Nickel catalysts, have been found to be useful for manufacturing polymer (P).

A negative electrode or anode material containing extractible metal may be employed so that extractible metal will be advantageously incorporated into the positive electrode during initial discharging.

A variety of materials can be used in negative electrodes or anodes in the metal or metal-ion cells of the present invention.

Selection of negative electrode or anode material will depends upon the nature of the metal or the metal-ion cell of the invention.

According to a first embodiment of the invention, the metal or the metal-ion cell is an alkaline or alkaline-earth secondary battery.

Representative negative electrodes materials of alkaline or alkaline-earth secondary batteries include:

- alkaline or alkaline-earth metal, including lithium, sodium, magnesium or calcium;
- graphitic carbons able to intercalate alkaline or alkaline-earth metal, typically existing in forms such as powders, flakes, fibers or spheres (for example, mesocarbon microbeads) hosting at least one alkaline or alkaline-earth metal;
- alkaline or alkaline-earth metal alloy compositions, including silicon-based alloys, germanium-based alloys;
- alkaline or alkaline-earth metal titanates, advantageously suitable for intercalating alkaline or alkaline-earth metal with no induced strain.

In a preferred variant of this embodiment, the metal or metal-ion cell is a Lithium secondary battery, wherein the negative electrode material is selected from the group consisting of:

- graphitic carbons able to intercalate lithium, typically existing in forms such as powders, flakes, fibers or spheres (for example, mesocarbon microbeads) hosting lithium;
- lithium metal;
- lithium alloy compositions, including notably those described in U.S. Pat. No. 6,203,944 (3M INNOVATIVE PROPERTIES CO) Mar. 20, 2001 and/or in WO 00/03444 (MINNESOTA MINING) Jun. 10, 2005;
- lithium titanates, generally represented by formula $Li_4Ti_5O_{12}$; these compounds are generally considered as "zero-strain" insertion materials, having low level of physical expansion upon taking up the mobile ions, i.e. $Li^+$;
- lithium-silicon alloys, generally known as lithium silicides with high Li/Si ratios, in particular lithium silicides of formula $Li_{4.4}Si$;
- lithium-germanium alloys, including crystalline phases of formula $Li_{4.4}Ge$.

The negative electrode may contain additives as will be familiar to those skilled in the art. Among them, mention can be made notably of carbon black, graphene or carbon nanotubes.

As will be appreciated by those skilled in the art, the negative electrode or anode may be in any convenient form including foils, plates, rods, pastes or as a composite made by forming a coating of the negative electrode material on a conductive current collector or other suitable support.

The charge-carrying electrolyte comprising a charge carrying medium and a metal salt advantageously provides a charge-carrying pathway between the positive and negative electrodes, and generally initially contains at least the charge carrying media and the metal salt.

The electrolyte may include other additives that will be familiar to those skilled in the art. As will be appreciated by those skilled in the art, the electrolyte may be in any convenient form including liquids and gels.

A variety of charge carrying media may be employed in the electrolyte. Exemplary media are liquids or gels (e.g. solvating polymers such as poly(oxyethylene)) capable of solubilizing sufficient quantities of metal salt and, optionally, other ingredients or additives, so that a suitable quantity of charge can be transported between the positive electrode and the negative electrode.

Exemplary charge carrying media can be used over a wide temperature range, for example, from about −30° C. to about 70° C. without freezing or boiling, and are stable in the electrochemical window within which the cell electrodes operate.

Representative charge carrying media include ethylene carbonate, propylene carbonate, dimethyl carbonate, diethyl carbonate, ethyl-methyl carbonate, butylene carbonate, vinylene carbonate, fluoroethylene carbonate, fluoropropylene carbonate, gamma-butyrolactone, methyl difluoroacetate, ethyl difluoroacetate, dimethoxyethane, diglyme (bis (2-methoxyethyl)ether), non-protonic ionic liquids, poly (oxyethylene)s and combinations thereof.

A variety of metal salts may be employed in the electrolyte. Metal salts which are stable and soluble in the chosen charge-carrying media will be generally selected for the metal-ion cell of the invention.

Metal salts suitable for the metal-ion cell of the invention are notably $M(PF_6)_n$, $M(BF_4)_n$, $M(ClO_4)_n$, M(bis(oxalato) borate)$_n$ ("M(BOB)$_n$"), $M[N(CF_3SO_2)_2]_n$, $M[N(C_2F_5SO_2)_2]_n$, $M[N(CF_3SO_2)(R_FSO_2)]_n$ with $R_F$ being $C_2F_5$, $C_4F_9$, $CF_3OCF_2CF_2$, $M(AsF_6)_n$, $M[C(CF_3SO_2)_3]_n$, with M being a metal, preferably a transition metal, an alkaline metal or an alkaline-earth metal, more preferably M=Li, Na, K, Cs, and n is the valence of said metal, typically n=1 or 2.

Among preferred lithium salts for Lithium-ion cells, mention can be made of $LiPF_6$, $LiBF_4$, $LiClO_4$, lithium bis(oxalato)borate ("LiBOB"), $LiN(CF_3SO_2)_2$, $LiN(C_2F_5SO_2)_2$, $M[N(CF_3SO_2)(R_FSO_2)]_n$ with $R_F$ being $C_2F_5$, $C_4F_9$, $CF_3OCF_2CF_2$, $LiAsF_6$, $LiC(CF_3SO_2)_3$ and combinations thereof.

The electrolyte can also conveniently contain at least one redox chemical shuttle. The electrolyte may however be formulated without dissolved redox chemical shuttle. The expression "redox chemical shuttle" refers to an electrochemically reversible compound that during charging of a lithium-ion cell can become oxidized at the positive electrode once the charging potential reaches a desired value, can migrate to the negative electrode, can become reduced at the negative electrode to reform the unoxidized (or less oxidized) shuttle species, and can migrate back to the positive electrode.

The metal or metal-ion cell of the invention may include a cell separator located between the positive and negative electrodes and through which charge-carrying species may pass.

Suitable separators will be familiar to those skilled in the art; porous separators or dense separators can be used.

According to a first embodiment of the invention, the metal-ion cell of the invention comprises a porous separator.

According to structure, separators of this embodiment can be divided as microporous membrane and nonwoven cloth. The former is a sheet, in which micro-size voids are introduced, while the latter is a felt or mat, in which fibers are randomly laid down to form numerous voids. The microporous membranes are featured by thinness (about 25 μm or less), small pore size (<1 μm) and high porosity (typically comprised between 40% and 70%). The nonwoven clothes are featured by thickness (80-300 μm), large pore size (10-50 μm), and higher porosity (60-80%).

Both natural and synthetic polymers can be used as the separator material in the rechargeable metal or metal-ion cell of the present invention. The natural materials mainly are celluloses and their chemically modified derivatives. The synthetic polymers include polyolefins, polyvinylidene fluoride, polytetrafluoroethylene, polyamide, polyvinyl alcohol, polyester, polyvinyl chloride, nylon, poly(ethylene terephthalate) and so forth. For specific needs of the rechargeable metal-ion cell of the invention, the separator or polymer material can be modified such as (1) applying a wetting agent to enhance initial wettability of the intrinsically hydrophobic separator and (2) chemically or physically grafting functional groups into polymer chains to increase permanent wettability of the separator or to give the separator special functions.

The microporous membranes are made either by a dry process or by a wet process. Both processes contain an extrusion step to produce a thin film and employ one or more orientation steps to generate pores. These processes are only applicable to molten or soluble polymers. The dry process generally consists of steps: (1) extruding molten polymer to form a film, (2) annealing the film, and (3) stretching the film to generate pores, while the wet process consists of (1) mixing with extractable additives to form a hot polymer solution, (2) extruding the hot solution to form a gel-like film, (3) extracting soluble additives out of the film to form porous structure. The membranes made by the dry process generally show distinct slit-pore microstructures, while these by the wet process exhibit interconnected spherical or elliptical pores. For the purpose of enhanced safety, two or more layers of membranes with different melting points can be laminated to make a thermal shutdown separator.

The nonwovens can be made through dry-laid process, we-laid process, spun-bond process or melt-blown process. All these processes consist of three steps: (1) making fabric webs, (2) bonding webs and (3) post-treatment, and in most cases the web making and bonding are done in one step. Among processes above, the wet-laid process has been widest used for the manufacture of battery separators.

According to a second embodiment of the invention, the separator is a dense separator.

The separator according to this embodiment is typically under the form of a gel consisting of a polymer component swelled by a charge carrying medium, as above detailed.

Among polymer components which can be used for providing a suitable gel separator, mention can be notably made of poly(meth)acrylonitrile polymers, polyalkyl(meth)acrylates, polysiloxanes, vinylidene fluoride polymers, poly(oxyethylene)s; all these polymers can be advantageously crosslinked.

In case of poly(oxyethylene)s, this polymer component can advantageously be used as charge carrying medium thanks to its solvating capabilities and simultaneously as polymer component, thanks to its mechanical properties, in particular when crosslinked; as a consequence, in this case, the dense separator might be mainly composed of said poly (oxyethylene)s containing solvated metal salt. Nevertheless, it can also be used in admixture with ionic liquids.

Certain N-substituted phenothiazine monomers, as above detailed and polymer comprising recurring units derived from the same, which are particularly suitable to the purposes of the present invention are also another object of the present invention.

The invention thus pertains to a N-substituted polyphenothiazine polymer [polymer (P)], comprising at least one N-substituted phenothiazine recurring unit of formula:

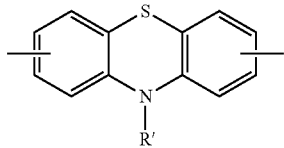

wherein R' is an electron-withdrawing group comprising at least one heteroatom selected from O, S, P and N, as above detailed.

Further, the invention relates to a monomer compound comprising at least one N-substituted phenothiazine moiety of formula:

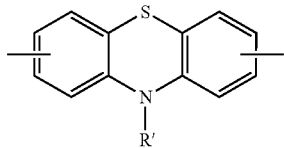

wherein R' is an electron-withdrawing group comprising at least one heteroatom selected from O, S, P and N, wherein said moiety additionally comprises at least one ionisable group preferably selected from carboxylate groups, sulphonate groups, sulphonylimide groups, phosphonate groups, with sulphonate and sulphonylimide groups being more preferred.

Other objects of the invention are monomers compound comprising at least one N-substituted phenothiazine moiety selected from the group consisting of:

(I) urethane-containing phenothiazine recurring units of formula:

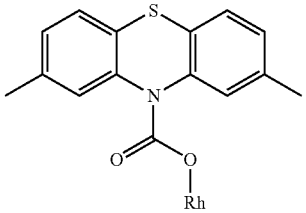

wherein Rh is a $C_1$-$C_{24}$ hydrocarbon group, possibly fluorinated, optionally comprising one or more heteroatoms comprised in an additional functional group;

(II) amide-containing phenothiazine recurring units of formula:

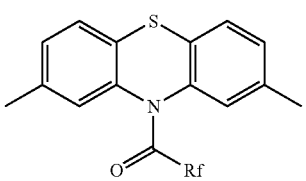

wherein Rf is a $C_1$-$C_{24}$ fluorinated hydrocarbon group, optionally comprising one or more heteroatoms comprised in an additional functional group.

Should the disclosure of any patents, patent applications, and publications which are incorporated herein by reference conflict with the description of the present application to the extent that it may render a term unclear, the present description shall take precedence.

The invention will be now described in more details with reference to the following examples whose purpose is merely illustrative and not intended to limit the scope of the invention.

Monomers Synthesis

Raw Materials

The starting commercially available compounds (Aldrich Acros) are phenothiazine (I) and 10H-methylphenothiazine (II).

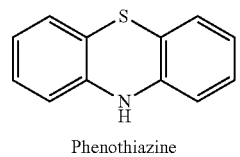

Phenothiazine

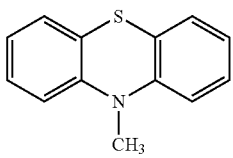

10H-methylphenothiazine

I) SYNTHESIS OF THE MONOMERS

Preparative Example I-1) of Comparison

Synthesis of 3,3'-dibromo-10H-methylphenothiazine III

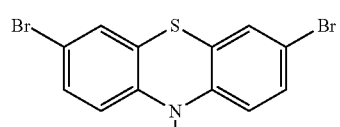

3,3'-dibromo-10H-methylphenothiazine

This compound was synthesized following procedures described in J-S. Kang, J-W. Park, J-H. Lee, S-Y. Oh/*Molecular Crystals and Liquid Crystals* 462, 2007, 267-276; M. Veld/*Molecular Materials and Nanosystems*, 2005.

To compound II (2.0 g; 9.4 mmol) in 50 mL DMF cold solution, three molar equivalent of N-bromosuccinimide (NBS) (1.7 g; 28 mmol) were added. The solution was maintained at 5 to 10° C. for one hour, then, at room temperature during 12 hours until starting material has been completely converted (checked by TLC using dichloromethane/pentane 1/5 as eluent). Then, the solvent was removed under reduced pressure and the solid residue was purified by chromatography on silica gel using dichloromethane/pentane 1/5 as eluent yielding to 3.3 g (yield 95%). The structure of compound III was confirmed by $^1$H and $^{13}$C NMR, IR and elemental analysis.

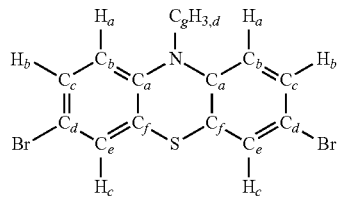

δ $^1$H NMR: 3.29 (H$_d$, s, 3H); 6.81 (H$_a$, d, 2H, $^3$J=8.7 Hz); 7.29 (H$_c$, d, 2H, $^4$J=2.3 Hz); 7.34 (H$_b$, dd, 2H, $^3$J=8.7 Hz, $^4$J=2.3 Hz).

δ $^{13}$C NMR: 36.24 (C$_g$, CH$_3$); 115.48 (C$_d$, CBr); 117.48 (C$_b$, CH); 125.56 (C$_f$, C); 130.01 (C$_e$, CH); 131.74 (C$_c$, CH); 145.92 (C$_a$, C).

IR: 2816, 3057 cm$^{-1}$ (C—H stretch), 1462 cm$^{-1}$ (C=C stretch), 1585 cm$^{-1}$ (CH$_2$ bend), 541 cm$^{-1}$ (C—Br stretch).

Elemental analysis: calc.: % C=42.1; % H=2.44; % N=3.77. found: % C=41.87; % H=2.44; % N=3.74.

Preparative Example I-2) of Comparison

Synthesis of 10H-ethylphenothiazine IV

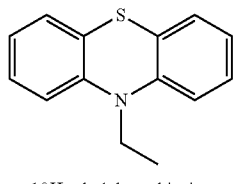

(IV)

10H-ethylphenothiazine

This compound was synthesized following procedures described in Y. S. Han, S. D. Kim, L. S. Park, D. U. Kim and Y. Kwon/*Journal of Polymer Science Part A Polymer Chemistry* 41, 2003, 2502-2511.

To compound I (5.0 g; 25 mmol) in 250 mL DMSO solution, 2.5 molar equivalents of potassium hydroxide (3.613 g; 64 mmol) were added. The solution was stirred at room temperature (R.T) for 30 min before the addition of 1.1 molar equivalent of 1-bromoethane (2.08 mL; 27 mmol). After refluxing for 24 hours, the solution was cooled to room temperature. The solution was poured into 300 mL of water, the obtained precipitate was filtered and extracted by dichloromethane (4×50 mL) in the presence of water (150 mL). The collected organic layer was dried with sodium sulfate, filtered and concentrated in vacuo. After purification by a silica gel column (eluent: pentane), the product was obtained as a light yellow powder in a 86% yield (4.9 g; 21.5 mmol). The structure of compound IV was confirmed by $^1$H and $^{13}$C NMR, IR and elemental analysis.

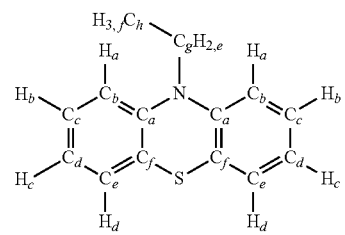

δ $^1$H NMR: 1.37 (H$_f$, t, 3H, $^3$J=6.9 Hz); 3.98 (H$_e$, q, 2H, $^3$J=6.9 Hz); 6.92 (H$_c$, dt, 2H, $^3$J=7.4 Hz, $^4$J=1.3 Hz); 7.00 (H$_a$, dd, 2H, $^3$J=8.2 Hz, $^4$J=1.3 Hz); 7.12 (H$_d$, dd, 2H, $^3$J=7.7 Hz, $^4$J=1.5 Hz); 7.18 (H$_b$, dt, 2H, $^3$J=7.4 Hz, $^4$J=1.5 Hz).

δ $^{13}$C NMR: 13.4 (C$_h$, CH$_3$); 42.3 (C$_g$, CH$_2$); 116.4 (C$_d$, CH); 123.3 (C$_b$, CH); 125.1 (C$_f$, C); 128.0 (C$_c$, CH), 128.4 (C$_e$, CH), 146.1 (C$_a$, C).

IR: 2949, 2970 cm$^{-1}$ (C—H stretch), 1590 cm$^{-1}$ (C=C stretch), 1459, 1321 cm$^{-1}$ (CH$_2$ and CH$_3$ bend).

Elemental analysis: calc. % C=73.97; % H=5.76; % N=6.16; % S=14.11. found: % C=73.96; % H=5.69; % N=6.17; % S=14.21.

Preparative Example I-3) of Comparison

Synthesis of 3,3'-dibromo-10H-ethylphenothiazine V

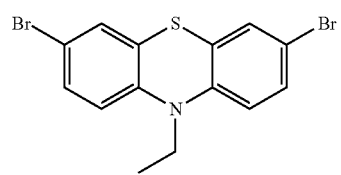

3,3'-dibromo-10H-ethylphenothiazine

The synthesis of V was carried out following procedure of preparative example I-1).

To compound IV (2.27 g; 10.0 mmol) in 100 mL freshly distilled DMF solution maintained at 5° C., 2.1 molar equivalent of NBS (3.78 g; 21.0 mmol) in 50 mL of freshly distilled DMF were added dropwise over a period of one hour. Then, the mixture was stirred at R.T for 12 hours until the starting material was completely converted (checked by TLC using ethyl acetate/hexane—1/5 as eluent). Then, the solvent was removed under reduced pressure and the crude product was purified by a silica gel column using ethyl acetate/hexane 1/5 as eluent yielding to 3.14 g (8.1 mmol; 81%). The structure of compound V was confirmed by $^1$H and $^{13}$C NMR, IR and elemental analysis.

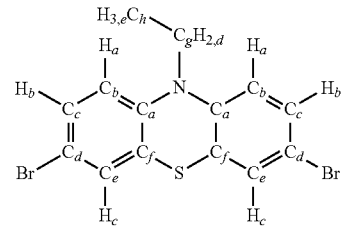

δ $^1$H NMR: 1.29 (H$_e$, t, 3H, $^3$J=6.9 Hz); 3.91 (H$_d$, q, 2H, $^3$J=6.9 Hz); 6.77 (H$_a$, d, 2H, $^3$J=8.7 Hz); 7.16 (H$_c$, d, 2H, $^4$J=2.3 Hz); 7.23 (H$_b$, dd, 2H, $^3$J=8.7 Hz, $^4$J=2.3 Hz).

δ $^{13}$C NMR: 13.2 (C$_h$, CH$_3$); 42.7 (C$_g$, CH$_2$); 115.3 (C$_d$, C—Br); 117.7 (C$_b$, CH); 126.6 (C$_f$, C); 130.1 (C$_e$, CH), 131.2 (C$_c$, CH), 144.7 (C$_a$, C).

IR: 2870, 2975 cm$^{-1}$ (C—H stretch), 1587 cm$^{-1}$ (C=C stretch), 1457, 1322 cm$^{-1}$ (CH$_2$ and CH$_3$ bend), 545 cm$^{-1}$ (C—Br stretch).

Elemental analysis: calc. % C=43.66; % H=2.88; % N=3.64; % S=8.33; % Br=41.50. found: % C=44.36; % H=2.74; % N=3.62; % S=6.80; % Br=36.71.

Preparative Example I-4) of Comparison

Synthesis of 10H-propylphenothiazine VI

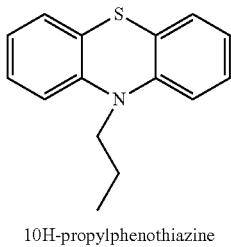

10H-propylphenothiazine

The synthesis of compound VI was carried out following procedure of preparative example I-2).

To compound I (6.0 g; 30 mmol) in 60 mL DMSO solution, six molar equivalents of potassium hydroxide (7.2 g; 180 mmol) were added. The solution was stirred at room temperature (R.T) for 30 min before the addition of 1.1 molar equivalent of 1-bromopropane (3.03 mL; 33 mmol). After 24 hours refluxing, the solution was cooled to room temperature. The solution was poured into 300 mL of water, the precipitate was filtered and extracted by dichloromethane (4×10 mL) in the presence of water (100 mL). The collected organic layer was dried with sodium sulfate, filtered and concentrated in vacuo. After purification by a silica gel column (eluent: hexane), the product was obtained as a light yellow powder in a 95% (6.9 g; 28.5 mmol) yield. The structure of VI was confirmed by $^1$H and $^{13}$C NMR, IR and elemental analysis.

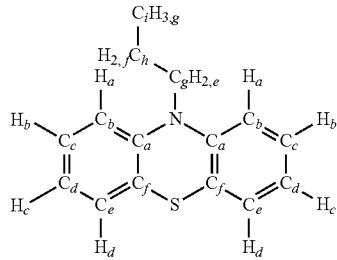

δ $^1$H NMR: 0.92 (H$_g$, t, 3H, $^3$J=7.2 Hz); 1.68 (H$_f$, tq, 2H, $^3$J=6.9 Hz et 7.2 Hz); 3.81 (H$_e$, t, 2H, $^3$J=6.9 Hz); 6.92 (H$_c$, dt, 2H, $^3$J=7.4 Hz); 6.99 (H$_a$, dd, 2H, $^3$J=7.9 Hz); 7.13 (H$_d$, dd, 2H, $^3$J=7.4 Hz); 7.18 (H$_b$, dt, 2H, $^3$J=7.9 Hz).

δ $^{13}$C NMR: 11.0 (C$_i$, CH$_3$); 19.5 (C$_h$, CH$_2$); 48.1 (C$_g$, CH$_2$); 115.8 (C$_d$, CH); 122.3 (C$_b$, CH); 123.6 (C$_f$, C); 127.0 (C$_c$, CH), 127.5 (C$_e$, CH), 144.7 (C$_a$, C).

IR: 754, 2924 cm$^{-1}$ (C—H stretch), 1591 cm$^{-1}$ (C=C stretch), 1457 cm$^{-1}$ (CH$_2$ bend).

Elemental analysis: calc.: % C=74.65; % H=6.26; % N=5.80; % S=13.29; % Br=41.50. found: % C=72.90; % H=6.06; % N=5.76; % S=13.57.

Preparative Example I-5) of Comparison

Synthesis of 3,3'-dibromo-10H-propylphenothiazine VII

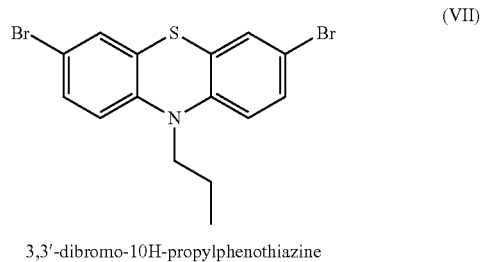 [SMILES: CCCN1c2ccc(Br)cc2Sc2cc(Br)ccc21]

3,3'-dibromo-10H-propylphenothiazine

This compound was synthesized following procedures described in M. Sailer, A. W. Franz, T. J. J. Müller/*Chemistry-A European Journal* 14, 2008, 2602-2614.

To compound VI (5.50 g; 22.8 mmol) in 10 mL freshly distilled acetic acid solution, one molar equivalent of bromine (1.17 mL; 22.8 mmol) was added dropwise. The mixture was stirred one hour before another portion of bromine (1.17 mL; 22.8 mmol) was added dropwise. After 18 hours of stirring and complete conversion of the starting material (checked by TLC using acetone/hexane—1/20 as eluent), 20 mL of satured aqueous solution of sulfite sodium and 20 mL of diethyl ether were added to the mixture and kept stirred for 2 hours. The aqueous layer was extracted with 3×15 mL of diethyl ether and the collected organic layer was concentrated in vacuo. After purification by a silica gel column using acetone/hexane 1/100 as eluent yielding, 8.65 g (21.7 mmol; 95%) of a light yellow powder. The structure of compound VII was confirmed by $^1$H and $^{13}$C NMR and IR and elemental analysis.

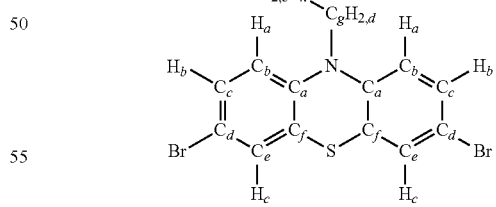

δ $^1$H NMR: 1.00 (H$_f$, t, 3H, $^3$J=7.4 Hz); 1.70 (H$_e$, hex, 2H, $^3$J=7.2 Hz); 3.69 (H$_d$, t, 2H, $^3$J=6.7 Hz); 6.63 (H$_a$, d, 2H, $^3$J=8.4 Hz); 7.18 (H$_c$, d, 2H, $^4$J=2.0 Hz); 7.21 (H$_b$, dd, 2H, $^3$J=8.4 Hz, $^4$J=2.0 Hz).

δ $^{13}$C NMR: 11.09 (C$_i$, CH$_3$); 19.70 (C$_h$, CH$_2$); 48.99 (C$_g$, CH$_2$); 114.46 (C$_d$, C—Br); 116.39 (C$_f$, C); 126.08 (C$_b$, CH); 129.31 (C$_e$, CH); 129.81 (C$_c$, CH); 143.69 (C$_a$, C).

IR: 2928 cm$^{-1}$ (C—H stretch), 1584 cm$^{-1}$ (C=C stretch), 1461 cm$^{-1}$ (CH$_2$ bend), 546 cm$^{-1}$ (C—Br stretch).

Elemental analysis: calc.: 45.14; % H=3.28; % N=3.51; % S=8.03; % Br=40.04. found: % C=45.19; % H=3.23; % N=3.72; % S=7.49; % Br=39.81.

Preparative Example I-6) of Comparison

Synthesis of 10H-heptylphenothiazine VIII

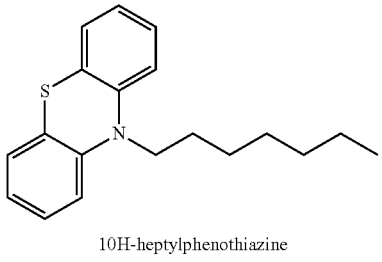

10H-heptylphenothiazine

The synthesis of compound VIII was carried out following procedure of preparative example I-2).

In a three necked flask, under argon, 10.0 g of compound I (50 mmol), 7.0 g of KOH (125 mmol) were dissolved in 150 mL dimethylsulfoxide (DMSO). Then, at room temperature, 1-bromoheptane (8.5 mL; 54 mmol) was added drop-wise. After refluxing during 24 hours said mixture, 200 mL of $H_2O$ were added, and crude product was extracted with 3 aliquots of 300 mL dichloromethane. The combined organic phases were dried on $Na_2SO_4$, and purified on silica gel (eluent: pentane) to yield compound VIII (yield 95%). The structure of compound VIII was determined by $^1H$ and $^{13}C$ NMR, IR and elemental analysis.

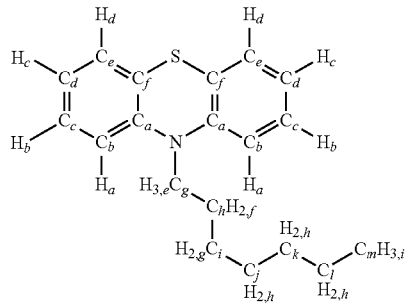

$\delta$ $^1H$ NMR: 0.87 ($H_i$, t, 3H, $^3J$=6.9 Hz et 6.8 Hz); 1.25-1.36 ($H_h$, m, 6H); 1.44 ($H_g$, quint, 2H); 1.81 ($H_f$, quint, 2H); 3.84 ($H_e$, t, 2H, $^3J$=7.2 Hz); 6.85-6.93 ($H_{a,c}$, m, 4H); 7.12-7.18 ($H_{d,b}$, m, 4H).

$\delta$ $^{13}C$ NMR: 15.56 ($C_m$, $CH_3$); 22.28 ($C_l$, $CH_2$); 26.50 ($C_i$, $CH_2$); 26.61 ($C_h$, $CH_2$); 28.69 ($C_j$, $CH_2$); 31.56 ($C_k$, $CH_2$); 46.81 ($C_g$, $CH_2$); 115.52 ($C_d$, CH); 122.16 ($C_b$, CH); 124.57 ($C_f$, C); 127.17 ($C_c$, CH); 126.99 ($C_e$, CH); 145.19 ($C_a$, C).

IR: 2854 et 3063 $cm^{-1}$ (C—H stretch),1573 $cm^{-1}$ (C═C stretch), 1455, 1371 $cm^{-1}$ ($CH_2$ and $CH_3$ bend).

Elemental analysis: calc.: % C=76.7; % H=7.79; % N=4.71. found: % C=77.06; % H=7.57; % N=4.76.

Preparative Example I-7) of Comparison

Synthesis of 3,3'-dibromo-10H-heptylphenothiazine IX

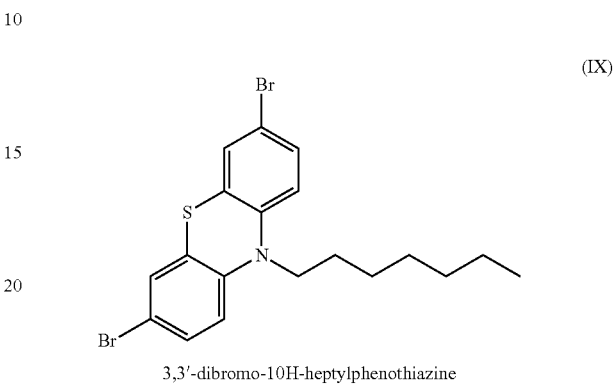

3,3'-dibromo-10H-heptylphenothiazine

The synthesis of compound IX was carried out following procedure of preparative example I-1).

To compound VIII (6.0 g; 20 mmol) in 40 mL $CH_2Cl_2$, three molar equivalent of N-bromosuccinimide (NBS) (3.6 g; 60 mmol) were added. The mixture was maintained under nitrogen atmosphere and stirring for one hour at 5 to 10° C. and then at room temperature for 12 hours. Reaction was followed by TLC (eluent: hexane, Rf: 0.85), until complete conversion of 10H-heptylphenothiazine. After removal of the solvent, the crude product was purified on silica gel using pentane as eluent to yield 8.23 g of compound IX as a yellow oily product (yield 90%). The structure of compound IX was determined by $^1H$ and $^{13}C$ NMR, IR and elemental analysis.

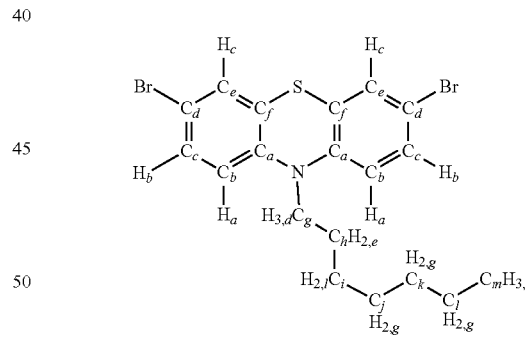

$\delta$ $^1H$ NMR: 0.82 ($H_h$, t, 3H, $^3J$=6.9 Hz); 1.25 ($H_g$, m, 6H); 1.39 ($H_f$, tt, 2H, $^3J$=6.9 et 7.4 Hz); 1.71 ($H_e$, tt, 2H, $^3J$=6.9 et 7.4 Hz); 3.82 ($H_d$, t, 2H, $^3J$=6.9 Hz); 6.85 ($H_a$, d, 2H, $^3J$=8.7 Hz); 7.20 ($H_c$, d, 2H, $^4J$=2.3 Hz); 7.27 ($H_b$, dd, 2H, $^3J$=8.7 Hz, $^4J$=2.3 Hz).

$\delta$ $^{13}C$ NMR: 14.43 ($C_m$, $CH_3$); 23.22 ($C_l$, $CH_2$); 27.35 ($C_i$, $CH_2$); 27.35 ($C_h$, $CH_2$); 29.60 ($C_j$, $CH_2$); 32.51 ($C_k$, $CH_2$); 48.06 ($C_g$, $CH_2$); 115.18 ($C_d$, C—Br); 118.17 ($C_b$, CH); 127.12 ($C_e$, CH); 130.11 ($C_f$, C); 131.15 ($C_c$, CH); 145.12 ($C_a$, C).

IR: 2850 et 2947 $cm^{-1}$ (C—H stretch), 1587 $cm^{-1}$ (C═C stretch), 1459, 1399 $cm^{-1}$ ($CH_2$ and $CH_3$ bend), 548 $cm^{-1}$ (C—Br stretch).

Elemental analysis: calc.: % C=50.1; % H=4.65; % N=3.08; % Br=35.1. found: % C=50.20; % H=4.73; % N=3.02; % Br=33.91%.

Preparative Example I-8) According to the Invention

Synthesis of 10H-methylcarboxylate-phenothiazine X

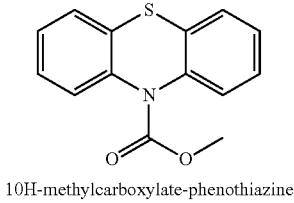

10H-methylcarboxylate-phenothiazine

This synthesis was carried out based on a procedure described in S. Darvesh, K. V. Darvesh, R. S. McDonald, D. Mataija, R. Walsh, S. Mothana, O. Lockridge, E. Martin/ *Journal of Medicinal Chemistry* 51(14), 2008, 4200-4212.

A 100 mL methanol containing carbonyl chloride-phenothiazine (1.00 g; 3.82 mmol) solution was maintained under reflux during 12 hours. After cooling, 30 mL of aqueous saturated $NaHCO_3$ were added. After removing the excess of methanol, residue was extracted with dichloromethane (3×30 mL). The purification over silica gel of combined organic extracts (eluent=3:10 dichloromethane:pentane) provided 0.585 g (yield 62%) of a product which was found by $^1H$ and $^{13}C$ NMR, IR and elemental analysis to comply with formula X.

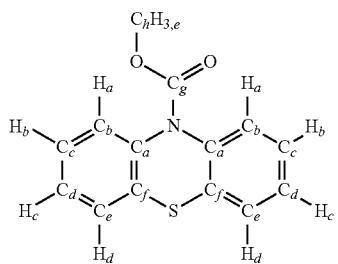

δ $^1H$ NMR: 3.73 ($H_e$, s, 3H); 7.22 ($H_c$, dt, 2H, $^3J$=7.6 Hz, $^4J$=1.3 Hz); 7.33 ($H_b$, dt, 2H, $^3J$=7.7 Hz, $^4J$=1.3 Hz); 7.41 ($H_a$, dd, 2H, $^3J$=7.8 Hz, $^4J$=1.5 Hz); 7.57 ($H_d$, dd, 2H, $^3J$=8.1 Hz, $^4J$=1.3 Hz).

δ $^{13}C$ NMR: 53.94 ($C_h$, $CH_3$); 127.50 ($C_c$, CH); 127.98 ($C_a$, CH); 128.07 ($C_b$, CH); 128.35 ($C_d$, CH); 132.81 ($C_e$, C); 139.33 ($C_f$, C); 154.67 ($C_g$, C).

IR: between 2850 and 3067 $cm^{-1}$ (C—H stretch), 1589 $cm^{-1}$ (C=C stretch), 1712 $cm^{-1}$ (C=O stretch), 1227 $cm^{-1}$ (C—C(O)—C stretch).

Elemental analysis: calc.: % C=65.4; % H=4.31; % N=5.44. found: % C=65.73; % H=4.26; % N=5.45.

Preparative Example I-9) According to the Invention

Synthesis of 10H-[1,1,1,2-tetrafluoro-3-oxopropane-2-lithium sulfonate]-phenothiazine XI

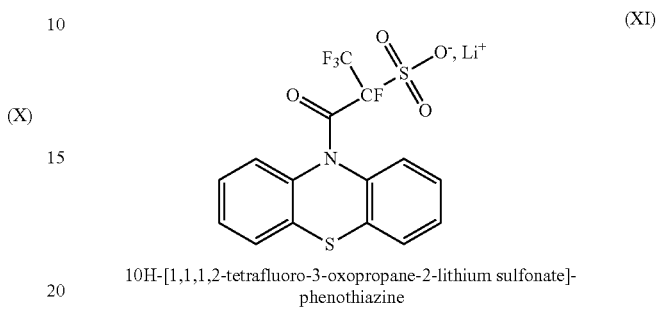

10H-[1,1,1,2-tetrafluoro-3-oxopropane-2-lithium sulfonate]-phenothiazine

This synthesis was carried out based on a procedure described in D. Benrabah, S. Sylla, J-Y. Sanchez, M. Armand/ *Journal of Power Sources* 54, 1995, 456-460.

Thus, under inert atmosphere, at −80° C., 1.1 molar equivalent of butyl-lithium (5.5 mmol) were added to a freshly distilled solution of diethyl ether (30 mL) containing 1.0 g of compound I (5.0 mmol). Then, a previously prepared solution of fluorinated sultone of formula FC(O)—CF($CF_3$)—$SO_2$F (0.7 mL; 5.0 mmol) in 10 mL diethyl ether was added dropwise. After one hour stirring, the resulting deeply black mixture was added of three molar equivalents of LiOH (629 mg; 15 mmol); after 24 hours at room temperature, a red solution was obtained. The mixture was thereafter concentrated (under reduced pressure) and filtered in under to remove the excess of LiOH. Finally, the residue was purified on silica gel (eluent: dichloromethane/ethyl acetate from 2/1 up to 2/3) to provide compound XI in a 7% yield. Structure of compound XI was then determined by $^1H$ and $^{13}C$ NMR, IR and elemental analysis.

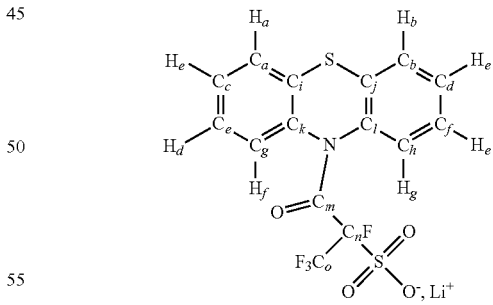

δ $^1H$ NMR: 7.30 ($H_c$, dt, 2H, $^3J$=7.7 Hz, $^4J$=1.1 Hz); 7.35-7.41 ($H_{d,e}$, m, 2H); 7.53 ($H_b$, dd, 1H, $^3J$=7.7 Hz, $^4J$=1.4 Hz); 7.57 ($H_a$, dd, 1H, $^3J$=7.7 Hz, $^4J$=1.4 Hz); 7.63 ($H_g$, dd, 1H, $^3J$=7.9 Hz, $^4J$=1.1 Hz); 8.09 ($H_f$, dd, 1H, $^3J$=7.9 Hz, $^4J$=1.1 Hz).

δ $^{13}C$ NMR: 100.99 ($C_n$, qd, CF—$CF_3$, $^1J$=244 Hz, $^2J$=29 Hz); 121.71 ($C_o$, dq, $CF_3$—CF, $^1J$=285 Hz, $^2J$=29 Hz); 127.87-128.90 ($C_{c-j}$, m, C); 134.20 ($C_{a,b}$, s, C); 139.03 ($C_l$, d, C, $^4J$=5.8 Hz); 139.41 ($C_k$, s, C); 161.57 ($C_m$, d, C, $^2J$=19 Hz).

δ $^{19}$F NMR: −157.23 (FC$_n$—C$_o$F$_3$, s); −72.75 (F$_3$C$_o$—C$_n$F, s).

IR: 2926, 3067 cm$^{-1}$ (C—H stretch), 1584 cm$^{-1}$ (C=C stretch), 1140 cm$^{-1}$ (S=O stretch), 760 cm$^{-1}$ (S—O stretch), 1673 cm$^{-1}$ (C=O stretch), 957, 1008, 1063 cm$^{-1}$ (C—F stretch), 3535 cm$^{-1}$ (O—H stretch, very hygroscopic product).

Elemental analysis: calc.: % C=43.6; % H=1.95; % N=3.39; % F=18.4; % C=38.95; % H=2.57; % N=3.08; % F=16.73 (one water molecule).

Preparative Example I-10) According to the Invention

Synthesis of 3,3'-dibromophenothiazine XII

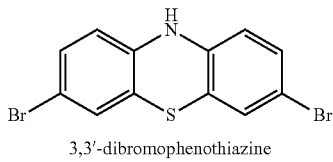

3,3'-dibromophenothiazine

The synthesis of compound XII was carried out following procedure of preparative example I-5).

To compound I (5.00 g; 25.0 mmol) in 300 mL freshly distilled acetic acid solution, 1.05 molar equivalent of bromine (1.35 mL; 26.35 mmol) was added dropwise. The mixture was stirred one hour before another portion of bromine (1.35 mL; 26.35 mmol) was added dropwise. After 18 hours of stirring and complete conversion of the starting material (followed by TLC using ethyl acetate/hexane—1.5/8 as eluent), 400 mL of satured aqueous solution of sulfite sodium and 200 mL of diethyl ether were added to the mixture and kept stirred for 2 hours. The aqueous layer was extracted with 5×50 mL of diethyl ether and the collected organic layer was concentrated in vacuo. The residue was washed with 5×20 mL of dichloromethane. Compound XII was obtained in the form of a light green powder with an 80% yield (7.17 g; 20 mmol).

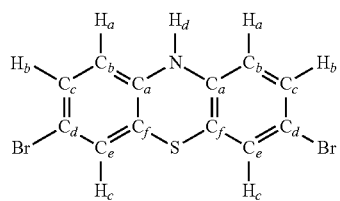

δ $^1$H NMR: 7.1 (H$_a$, d, 1H, $^3$J=8.4 Hz); 7.5 (H$_c$, d, 1H, $^4$J=2.0 Hz); 7.6 (H$_b$, dd, 1H, $^3$J=8.4 Hz, $^4$J=2.0 Hz); 8.5 (H$_d$, s, 1H).

δ $^{13}$C NMR: 123.9 (C$_d$, C); 126.7 (C$_b$, CH); 129.7 (C$_f$, C); 139.0 (C$_e$, CH); 140.9 (C$_c$, CH); 151.9 (C$_a$, C).

IR: 3020 cm$^{-1}$ (C—H stretch), 1462 cm$^{-1}$ (C=C stretch), 3323 cm$^{-1}$ (N—H stretch), 548 cm$^{-1}$ (C—Br stretch).

Elemental analysis: calc. % C=40.76; % H=1.98; % N=3.92; % S=8.98; % Br=44.76. found: % C=39.89; % H=1.65; % N=3.80; % S=8.68; % Br=42.21.

Preparative Example I-11) According to the Invention

Synthesis of 3,3'-dibromo-10H-(lithium propanesulfonate)-phenothiazine XIII

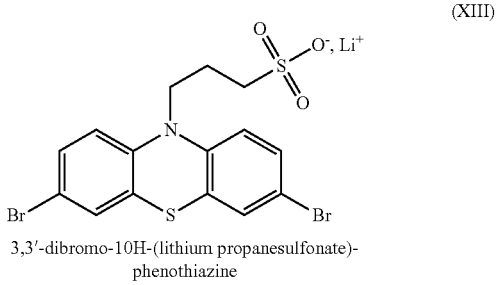

3,3'-dibromo-10H-(lithium propanesulfonate)-phenothiazine

This compound was synthesized following procedures described in E. Marzocchi, S. Grilli, L. Della-Ciana, L. Prodi, M. Mirasoli, A. Roda/Analytical biochemistry 377, 2008, 189-194.

To compound XII (504 mg; 1.41 mmol) in 40 mL freshly distilled THF solution at −80° C., 1.05 molar equivalent of BuLi (2.5 M in hexane) (588 µL; 1.48 mmol) was added dropwise. The solution was kept at −80° C. over 20 min and then was allowed to reach R.T within a one hour stirring before one molar equivalent of freshly distilled 1,3-propanesultone (124 µL; 1.4 mmol) was added dropwise at 0° C., this was followed by a 30 min stirring at the same temperature. After 24 hours of R.T stirring, the mixture was heated to 90° C. for 12 hours. The precipitate was filtered and washed with warm dichloromethane, giving a light blue powder with a 26% yield (178 mg; 0.37 mmol).

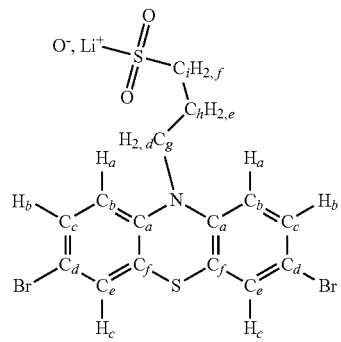

δ $^1$H NMR: 1.9 (H$_f$, t, 2H, $^3$J=6.9 Hz); 2.5 (H$_e$, tt, 2H, $^3$J=6.9 Hz); 3.9 (H$_d$, t, 2H, $^3$J=6.9 Hz); 7.0 (H$_a$, d, 1H, $^3$J=9.5 Hz); 7.3 (H$_c$, d, 1H, $^4$J=2.3 Hz); 7.3 (H$_b$, dd, 1H, $^3$J=9.5 Hz, $^4$J=2.3 Hz).

δ $^{13}$C NMR: 22.4 (C$_h$, CH$_2$); 45.9 (C$_g$, CH$_2$); 48.3 (C$_i$, CH$_2$); 113.9 (C$_d$, C); 117.6 (C$_f$, C); 125.0 (C$_b$, CH); 128.9 (C$_e$, CH); 130.3 (C$_c$, CH); 143.6 (C$_a$, C).

IR: 2924 cm$^{-1}$ (C—H stretch), 1580 cm$^{-1}$ (C=C stretch), 1456, 1386 cm$^{-1}$ (CH$_2$ and CH$_3$ bend), 1190, 1658 cm$^{-1}$ (S=O and S—O stretch), 542 cm$^{-1}$ (C—Br stretch), 3435 cm$^{-1}$ (O—H stretch, very hygroscopic product).

Elemental analysis: calc.: % C=37.14; % H=2.49; % N=2.89; % O=9.89; % S=13.22; % Br=44.76. found: % C=35.84; % H=2.88; % N=2.65; % O=13.32; % S=12.00 (one water molecule).

II) ELECTROCHEMICAL INVESTIGATION ON SUBSTITUTED PHENOTHIAZINE MONOMERS

Determinations were carried out in $CH_3CN+0.1$ M tetrabutyl ammonium perchlorate (TBAP) solutions. The reference electrode used was $Ag/AgNO_3$ (0.01 M) in $CH_3CN+0.1M$ TBAP, being understood that potentials can be converted to SHE scale by adding 0.548 V as described in V. Pavlishchuk et al., *Inorg. Chimica Acta* 298, 2000, 97-102 and to $Li/Li^+$ by adding 3.588 V (E ($Li/Li^+$)=-3.04 V vs SHE). The working electrode was in certain cases platinum and in other cases vitreous carbon. Nevertheless, no significant dependency of $E^{1/2}$ value upon choice of working electrode was observed, so that it is reasonable to conclude that $E^{1/2}$ value so determined are substantially independent from the working electrode used for their determination. In all cases, the cyclic voltammetry (100 $mV·s^{-1}$) exhibits two successive reversible one-electron oxidation processes in the anodic region, whereas no reduction peak was detected up to -2.5 V. So obtained experimental data are summarized in the above table.

As herein used, $E^{1/2}$ represents the half-wave potential (in French, "potentiel de demi-vague") associated with a certain redox system of a certain compound. Phenothiazine-based compounds have two different redox systems which proved to be advantageous for the present invention; the half-wave potentials associated with these redox systems are herein named $E^{1/2}_1$ and $E^{1/2}_2$ respectively.

FIG. 1 depicts the cyclic voltammetry trace recorded for compound II (1.7 mM) in $CH_3CN$+TBAP 0.1 M solution on a platinum electrode (5 mm), at a scan rate of v=100 $mV·sec^{-1}$.

FIG. 2 depicts the cyclic voltammetry trace recorded for compound XI (3.9 mM) in $CH_3CN$+TBAP 0.1 M solution on a platinum electrode (5 mm), at a scan rate of v=100 $mV·sec^{-1}$.

FIG. 3 depicts the cyclic voltammetry trace recorded for compound VI (5.97 mM) in $CH_3CN$+TBAP 0.1 M solution on a platinum electrode (2 mm), at a scan rate of v=100 $mV·sec^{-1}$.

FIG. 4 depicts the cyclic voltammetry trace recorded for compound VII (4.89 mM) in $CH_3CN$+TBAP 0.1 M solution on a platinum electrode (2 mm), at a scan rate of v=100 $mV·sec^{-1}$.

FIG. 5 depicts the cyclic voltammetry trace recorded for compound XIII (0.5 mM) in $CH_3CN$+TBAP 0.1 M solution on a platinum electrode (2 mm), at a scan rate of v=100 $mV·sec^{-1}$.

Comparison of these $E^{1/2}$ values showed that achievement of high oxidation potentials could be obtained only when phenothiazine moiety was N-substituted with an electron-withdrawing group comprising at least one heteroatom selected from O, S, N, P. Actually, the more donor substituent (heptyl for compound VIII) led to the less positive $E^{1/2}$ values whereas for carbonyl substituted phenothiazine $E^{1/2}$ values increased up to reach close to 1 V vs $Ag/Ag^+$.

While reversibility of first oxidation was confirmed, no definitive conclusion was obtained regarding possible reversibility of second oxidation step. As a matter of fact, side reactions, including parasite phenomena due to electrolyte moisture might explain obtained results. Nevertheless, according to the value in Table 1 of the voltage difference between the two redox systems ($\Delta E^{1/2}$) of the compounds, it appeared that the second redox system proved to be reversible (at 100 $mV·s^{-1}$) as long as this difference is higher than 600 mV.

Indeed, further study of the second redox system of compound I was carried out, yielding to the result that, in presence of water, the reversibility of the said redox system was compromised. This could be explained by the formation of dication diradical, during that second oxidation, increasing the acid power of the amine proton, leading to his unhooking and thus the degradation of the compound by formation of by-products.

Hence, we could explain the irreversibility of its dibromine derivative, the compound XII. Furthermore, the synthesis of two compounds with an electron-withdrawing group, an ester (X) and a perfluorated salt lithium (XI) proved to be irreversible in the conditions of our experimentation. Thus, given the reversible property of the redox system of the alkyl group phenothiazine derivatives, an alkyl root electron-withdrawing group (XIII) was attached to the phenothiazine in order to preserve the global reversibility of the two redox systems. The reversibility of the redox systems of compound XII was indeed kept thanks to the sufficient spacer length between the sulfonate group and the molecule core. The said compound is a good applicant for the copolymerisation with alkylphenothiazine in order to synthesize a polymer with good mechanical properties and ionic conductivity.

TABLE 1

| Compound | $E^{1/2}_1$ 1st system (V vs SHE) | $\Delta E$ (mV) | $E^{1/2}_2$ 2nd system (V vs SHE) | $\Delta E$ (mV) | $\Delta E^{1/2}$ (mV) |
|---|---|---|---|---|---|
| I | 0.982 | 103 | 1.376 | 160 | 0.394 |
| II | 0.973 | 135 | 1.627 | 137 | 0.654 |
| III | 1.089 | 100 | 1.700 | 101 | 0.611 |
| IV | 0.932 | 106 | 1.603 | 123 | 0.671 |
| V | 1.052 | 93 | 1.664 | 133 | 0.612 |
| VI | 0.930 | 117 | 1.597 | 103 | 0.667 |
| VII | 1.062 | 95 | 1.677 | 106 | 0.615 |
| VIII | 0.926 | 108 | 1.595 | 103 | 0.669 |
| IX | 1.050 | 82 | 1.667 | 95 | 0.617 |
| X | 1.545 | 137 | 1.776 | 137 | 0.231 |
| XI | 1.608 | 68 | 1.814 | 61 | 0.206 |
| XII | 0.980 | 110 | 1.375 | 160 | 0.395 |
| XIII | 1.038 | 105 | 1.690 | 162 | 0.652 |

III) POLYMERIZATION OF PHENOTHIAZINE MONOMERS

III)-1) Polymerization of Compound XII by Microwave Assisted Suzuki Coupling to Yield Poly(I)—of Comparison

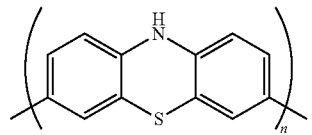

The Poly(I) was synthesized following procedures described in A. Tsami, X. H. Yang, T. Farrell, D. Neher, E. Holder/*Journal of Polymer Science Part A: Polymer Chemistry* 46, 2008, 7794-7808; M. Melucci, G. Barbarella, G. Sotgiu/*The Journal of Organic Chemistry* 67, 2002, 8877-8884; A. Britze, J. Jacob, V. Choudhary, V. Moellmann, G. Grundmeier, H. Luftmann, D. Kuckling/*Polymer* 51, 2010, 5294-5303.

To 5 mL of freshly distilled dimethylacetamide, 143 mg of compound XII (0.4 mmol), one molar equivalent of bispinacolatodiboron (104 mg; 0.4 mmol), 5 molar equivalent of fluoride potassium (117 mg; 2.0 mmol) and 4% molar of [1,1-Bis(diphenylphosphino)ferrocene]dichloropalladium (II) (PdCl$_2$dppf) (11.7 mg; 1.6·10$^{-2}$ mmol) were added. The mixture was submitted to microwave treatment (150 Watts) during 15 min leading to a black solution. After cooling, polymer was precipitated by addition of 50 mL of water. Purification and dissolution of the polymeric material were carried out in methanol. This led to only 16 mg of soluble chains (20% yield) the main part of the crude material being insoluble in numerous solvents. This soluble part was analysed by GPC with a polystyrene equivalent and showed a weight average molecular weight of 2229 g·mol$^{-1}$, and a number average degree of polymerization of about 9 (i.e. 9 patterns similar to compound I). The polymer was characterized by IR and elemental analysis.

IR: 2922 cm$^{-1}$ (C—H stretch), 1618 cm$^{-1}$ (C=C stretch).

Elemental analysis: calc.: % C=73.07; % H=3.58; % N=7.10; % S=16.26. found: % C=62.93; % H=5.29; % N=4.70; % S=8.80.

As observed for all the polymers synthesized using this procedure, elemental analysis showed sometimes some differences between the calculated and the found analysis; without being bound by any theory, the Applicant believes that these differences might result from the presence of some mineral contribution as palladium salt.

III-2) Polymerization of Compound III by Suzuki Coupling to Yield Poly(II)—of Comparison

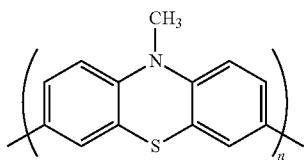

III-2-a) Run without Microwave

Poly(II$_a$) was synthesized following procedures described in A. R. Rabindranath, Y. Zhu, I. Heim, B. Tieke/*Macromolecules* 39, 2006, 8250-8256.

To 5 mL freshly distilled DMF, PdCl$_2$(II) and (3.0 mg; 0.017 mmol) diphenylphosphineferrocene (9.8 mg; 0.017 mmol) were added. After 15 minutes at 50° C., a clear orange solution was obtained. Compound III (300 mg; 0.81 mmol), bis(pinacolato)diboron (209 mg; 0.81 mmol) and triethylamine (1.7 equivalents; 195 mL; 1.38 mmol) were then added. The resulting solution was heated at 100° C. during 12 hours. Further to the addition of 6 mL H$_2$O, 469 mg sodium bicarbonate (5.59 mmol) and THF (15 mL), the mixture was maintained under reflux during additional 48 h. Solvent was then removed under vacuum; residue, upon addition of 50 mL H$_2$O, was extracted several times with CH$_2$Cl$_2$. Combined organic extracts were reduced in volume down to 20 mL, and 150 mL methanol were added enabling precipitation of the polymer. After filtration and washing with methanol, 120 mg of polymer as a black powder, were obtained (yield 70%), which was characterized by IR analysis.

IR: 2800, 3000 cm$^{-1}$ (C—H stretch), 1458 cm$^{-1}$ (C=C stretch), and fading of the C—Br (stretch at 541 cm$^{-1}$).

III-2-b) Run Under Microwave

The synthesis of Poly(II$_b$) was carried out following procedure described in M. Melucci, G. Barbarella, M. Zambianchi, P. Di Pietro, A. Bongini/*Journal of Organic Chemistry* 69, 2004, 4821-4828.

To 10 mL freshly distilled toluene, PdCl$_2$(II) (2.1 mg; 0.012 mmol) and diphenylphosphineferrocene (6.6 mg; 0.012 mmol) were added. After 15 minutes at 50° C., a clear orange solution was obtained. Then, KF (77 mg; 1.32 mmol), compound III (100 mg; 0.27 mmol), bis(pinacolato)diboron (70 mg; 0.27 mmol), 2 mL methanol and 10 mL DMF were added to said solution. The mixture was submitted to microwave treatment (130 Watts) during 10 minutes leading to a black solution. After cooling, polymer was precipitated by addition of 100 mL methanol. 46 mg of a black polymer were obtained (yield 80%), and analyzed by IR.

IR: the IR spectrum exhibited the same characteristics as those obtained using a run without microwave.

III-2-c) Run Under Microwave

The synthesis of Poly(II$_c$) was carried out following procedure described in III-2-b) (Poly(II$_b$)).

To 5 mL of freshly distilled dimethylacetamide, 148 mg of compound III (0.4 mmol), one molar equivalent of bispinacolatodiboron (104 mg; 0.4 mmol), 5 molar equivalent of fluoride potassium (117 mg; 2.0 mmol) and 4% molar of PdCl$_2$dppf (11.7 mg; 1.6·10$^{-2}$ mmol) were added. The mixture was submitted to microwave treatment (150 Watts) during 15 min leading to a black solution. After cooling, polymer was precipitated by addition of 50 mL of water. Purification and dissolution of the polymeric material have been carried out in methanol. This led to only 17 mg of soluble chains (20% yield) the main part of the crude material being insoluble in numerous solvents. This soluble part was analysed by GPC with a polystyrene equivalent and showed a weight average molecular weight of 2302 g·mol$^{-1}$ and a number average degree of polymerization of about 8 (i.e. about 8 patterns similar to compound II). The polymer was characterized by IR and elemental analysis.

IR: 2923 cm$^{-1}$ (C—H stretch), 1636 cm$^{-1}$ (C=C stretch), 1463 cm$^{-1}$ (CH$_3$ bend).

Elemental analysis: calc.: % C=73.90; % H=4.29; % N=6.63; % S=15.18. found: % C=63.91; % H=4.16; % N=5.66; % S=11.08.

III-3) Polymerization of Compound V by Suzuki Coupling to Yield Poly(IV)—of Comparison

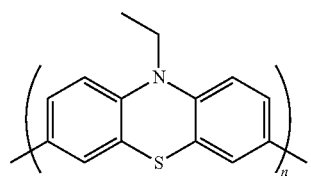

The synthesis of Poly(IV) was carried out following procedure of preparative example III-1).

To 5 mL of freshly distilled dimethylacetamide, 154 mg of V (0.4 mmol), one molar equivalent of bispinacolatodiboron (104 mg; 0.4 mmol), 5 molar equivalent of fluoride potassium (117 mg; 2.0 mmol) and 4% molar of PdCl$_2$dppf (11.7 mg; 1.6·10$^{-2}$ mmol) were added. The mixture was submitted to microwave treatment (150 Watts) during 15 min leading to a black solution. After cooling, polymer was precipitated by addition of 50 mL of water. Purification and dissolution of the polymeric material were carried out in methanol. This led to only 18 mg of soluble chains (20% yield), the main part of the crude material being insoluble in numerous solvents. This soluble part was analysed by GPC with a polystyrene equivalent and showed a weight average molecular weight of 2350 g·mol$^{-1}$ and a number average degree of polymerization of about 7 (i.e. about 7 patterns similar to compound IV). The polymer was characterized by IR and elemental analysis.

IR: 2924 cm$^{-1}$ (C—H stretch), 1639 cm$^{-1}$ (C=C stretch), 1462 cm$^{-1}$ (CH$_3$ bend).

Elemental analysis: calc.: % C=74.63; % H=4.92; % N=6.22; % S=14.23. found: % C=62.03; % H=4.33; % N=5.44; % S=10.16.

III-4) Polymerization of Compound VII by Microwave Assisted Suzuki Coupling to Yield Poly(VI)—of Comparison

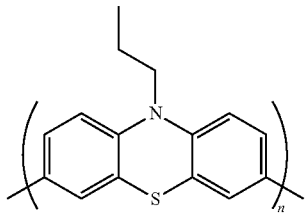

The synthesis of Poly(VI) was carried out following procedure of preparative example III-1).

To 5 mL of freshly distilled dimethylacetamide, 200 mg of compound VII (0.5 mmol), one molar equivalent of bispinacolatodiboron (130 mg; 0.5 mmol), 5 molar equivalent of fluoride potassium (147 mg; 2.5 mmol) and 4% molar of PdCl$_2$dppf (14.6 mg; 2.0·10$^{-2}$ mmol) were added. The mixture was submitted to microwave treatment (150 Watts) during 15 min leading to a black solution. After cooling, polymer was precipitated by addition of 20 mL of water. The precipitate was filtered and washed with methanol. To the residue was added 20 mL of dichloromethane and 10 mL of methanol, the mixture was stirred over 20 min and warmed at 50° C. Then, the mixture was evaporated and to the residue were added 5 mL of acetone, 5 mL of methanol and 5 mL of a 33% aqueous solution of HCl. After the evaporation of the solvents, 40 mL of water were added and the aqueous layer was extracted with 5×15 mL of dichloromethane. The organic layer was dried by sodium sulfate, filtered, and concentrated in vacuo. The polymer was analysed by GPC with a polystyrene equivalent and showed a weight average molecular weight of 2000 g·mol$^{-1}$ and a number average degree of polymerization of about 6 (i.e. about 6 patterns similar to compound VI). The polymer was characterized by RMN, IR and elemental analysis.

δ $^1$H NMR: the signature fitted the VII's one but we noted the presence of boronic acid pinacol ester (polymer terminal chains position) with the H$_3$C signature at 1.17 ppm.

δ $^{13}$C NMR: the signature fitted the VI's one but we noted the presence of boronic acid pinacol ester (polymer terminal chains position) with the C—H$_3$ signature at 24.7 ppm.

δ $^{11}$B NMR: confirmation of the presence of boronic acid attached in the extremities of the polymer with the peak at 30 ppm (the $^{11}$B nmr signature of the bispinacolatodiboron appeared at 22 ppm).

IR: 2963 cm$^{-1}$ (C—H stretch), 1599 cm$^{-1}$ (C=C stretch), 1353, 1456 cm$^{-1}$ (CH$_3$ and CH$_2$ bend).

Elemental analysis: calc.: % C=75.28; % H=5.47; % N=5.85; % S=13.40. found: % C=57.51; % H=4.64; % N=4.13; % S=8.56.

III-5) Polymerization of Compound IX to Yield Poly(VIII) Polymer—of Comparison

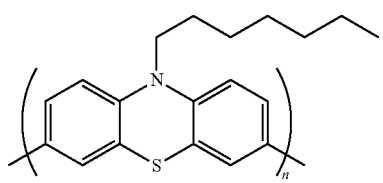

III-5-a) by Yamamoto Coupling

The synthesis of Poly(VIII$_a$) was carried out following procedure described in T. Yamamoto, A. Morita, Y. Miyazaki, T. Maruyama, H. Wakayama, Z. H. Zhou, Y. Nakamura, T. Kanbara, S. Sasaki, K. Kubota/*Macromolecules* 25, 1992, 1214-1223; T. Yamamoto, Y. Hayashi, A. Yamamoto/*Bulletin of the Chemical Society of Japan* 51(7), 1978, 2091-2097.

This reaction was carried out in drastic anhydrous condition; to ensure the same, all compounds and solvents were dried by distillation for liquids or under vacuum for solids. In a flask, under inert atmosphere, bis(1,5-cyclooctadienyl) nickel$^{(0)}$ (Ni(COD)$_2$) (530 mg; 2 mmol), 2,2-bipyridine (bpy) (312 mg; 2 mmol) and 1,5-cyclooctadiene (COD) (300 µL, 2 mmol) were solubilised in a mixture of DMF (20 mL) and toluene (20 mL). Mixture was heated at 80° C. for 30 minutes; then, compound IX (911 mg; 2 mmol) was added and reaction mixture maintained at 80° C. for additional 72 hours. Bromopentafluorobenzene (0.1% compared to the monomer) was finally added to quench the polymerization. Concentrated HCl (10 mL), methanol (10 mL) and acetone (10 mL) were then added to the reaction mixture so as to ensure precipitation of the polymer. Solid residue was then solubilised in CH$_2$Cl$_2$; said solution was then dried over Na$_2$SO$_4$; removal of the solvent under vacuum yielded to a solid polymeric residue (yield 80%), which was characterized by GPC, $^1$H and $^{13}$C NMR, IR and elemental analysis. GPC analysis provided evidence of a M$_w$ of about 5500 g·mol$^{-1}$ and a number average degree of polymerization of about 13 (corresponding to about 13 patterns of compound VIII).

δ $^1$H NMR: broad signals of the phenothiazine moieties were observed.

δ $^{13}$C NMR: broad signals of the phenothiazine moieties were observed.

IR: 2849 et 2950 cm$^{-1}$ (C—H stretch), 1456 cm$^{-1}$ (C—C et C=C stretch), 1580 et 729 cm$^{-1}$ (CH$_2$ bend), 1377 cm$^{-1}$ (CH$_3$ bend).

Elemental analysis: calc. % C=77.29; % H=7.12; % N=4.74. found: % C=77.11; % H=7.21; % N=4.68.

III-5-b) by Suzuki Coupling

The synthesis of Poly(VIII$_b$) was carried out following procedure of preparative example III-1).

To 5 mL of freshly distilled dimethylacetamide, 364 mg of compound IX (0.8 mmol), one molar equivalent of bispinacolatodiboron (207 mg; 0.8 mmol), 5 molar equivalent of fluoride potassium (235 mg; 4.0 mmol) and 4% molar of PdCl$_2$dppf (23.4 mg; 3.2·10$^{-2}$ mmol) were added. The mixture was submitted to microwave treatment (150 Watts) during 15 min leading to a black solution. After cooling, polymer was precipitated by addition of 20 mL of water. The precipitate was filtered and washed with water and methanol. To the residue was added 20 mL of acetone, 20 mL of methanol and 20 mL of a 33% aqueous solution of HCl. The precipitate was filtered and dried in vacuo. The polymer was analysed by GPC with a polystyrene equivalent and showed an average molecular weight of 2300 g·mol$^{-1}$ and a number average degree of polymerization of about 6 (which corresponds to approximately 6 patterns similar to compound VIII). The polymer was characterized by RMN, IR and elemental analysis.

δ $^1$H NMR: the signature fitted the IX's one but we can notice the presence of boronic acid pinacol ester (polymer terminal chains position) with the H$_3$_C signature at 1.24 ppm.

δ $^{13}$C NMR: the signature fitted the VIII's one but we can notice the presence of boronic acid pinacol ester (polymer terminal chains position) with the C—H$_3$ signature at 24.8 ppm.

δ $^{11}$B NMR: confirmation of the presence of boronic acid attached in the extremities of the polymer with the peak at 30 ppm.

IR: 2849, 2950 cm$^{-1}$ (C—H stretch), 1580 cm$^{-1}$ (C=C stretch), 1377, 1456 cm$^{-1}$ (CH$_3$ and CH$_2$ bend).

Elemental analysis: calc.: % C=77.24; % H=7.16; % N=4.74; % S=10.85. found: % C=66.00; % H=6.58; % N=3.30; % S=6.91.

IV) ELECTROCHEMICAL BEHAVIOUR OF THE POLYMERS

The investigations were carried out in CH$_3$CN+0.1 M tetrabutyl ammonium perchlorate (TBAP) solution. The reference electrode used was Ag/AgNO$_3$ (0.01 M) in CH$_3$CN+0.1 M TBAP. Polymer was deposited on the electrode surface by dip coating. Prior to analysis, polymeric material was dissolved in organic medium (i.e. THF, CH$_2$Cl$_2$, 1,2-dichloroethane . . . ), and one drop of the mixture was casted on the electrode surface and solvent was removed under vacuum.

IV-1) Electrochemical Behaviour of Poly(VIII$_b$) in CH$_3$CN+0.1 M TBAP—of Comparison FIG. 7 shows the cyclic voltammetry trace of a film of Poly(VIII$_b$) casted from a CH$_2$Cl$_2$ solution on a Pt electrode (diameter=5 mm) in CH$_3$CN+0.1 M tetrabutyl ammonium perchlorate (TBAP) solution, at a scan rate V=10 mV·sec$^{-1}$.

As shown in FIG. 7, electrochemical behaviour of Poly (VIII$_b$) was essentially similar to that of corresponding compound VIII. The redox process was found to be reversible (ΔEp close to 100 mV) whereas E$^{1/2}$ value was strictly close to the one of compound VIII, demonstrating that the extension of the electronic delocalisation due to polymerisation did not induce important modification of the electrochemical behaviour of the redox centre. Moreover, the charge consumed during the oxidation and reduction steps were consistent with the amount of the polymer deposited on the electrode surface.

IV-2) Electrochemical Behaviour of Poly(II$_c$) in CH$_3$CN+0.1 M TBAP—of Comparison FIG. 6 showed the cyclic voltammetry trace of a film of Poly(II$_c$) (3·10$^{-5}$ mol) casted from a CH$_2$Cl$_2$ solution on a Pt electrode (diameter=5 mm) in CH$_3$CN+0.1 M tetrabutyl ammonium perchlorate (TBAP) solution, at a scan rate V=2 mV·sec$^{-1}$.

As illustrated by FIG. 6, the cyclic voltammetry trace of Poly(II$_c$) showed that the E$^{1/2}$ value is consistent with that of compound II, corroborating the thesis that, as previously observed for Poly(VIII$_b$), the extension of the electronic delocalisation within the polymer did not affect the electrochemical behaviour of II.

IV-3) Electrochemical Behaviour of the Other Polymers Synthesized

The other synthesized polymers proved to maintain the highness of their redox potential.

V) ADDITIONAL EXAMPLES OF SYNTHESIS

V-1) Synthesis of Poly(VI-XIII')

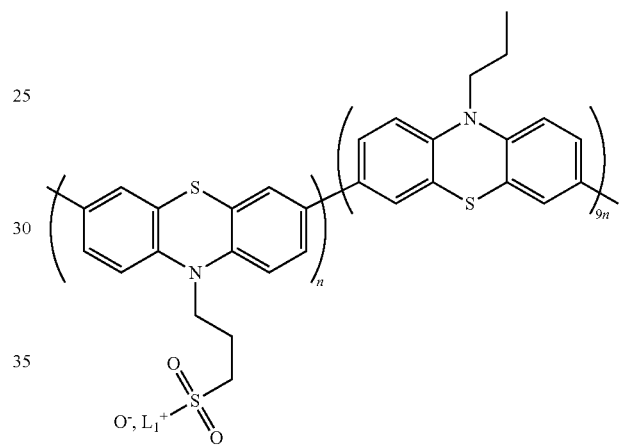

The synthesis of Poly(VI-XIII') is carried out following procedure of preparative example III-1).

To 5 mL of freshly distilled dimethylacetamide, about 0.9 molar equivalent of compound VII (0.72 mmol), about 0.1 molar equivalent of compound XIII (39 mg; 0.08 mmol), one molar equivalent of bispinacolatodiboron (207 mg; 0.8 mmol), 4 molar equivalent of lithium hydroxide (136 mg; 3.2 mmol) and 4% molar of PdCl$_2$dppf (23.4 mg; 3.2·10$^{-2}$ mmol) are added. The mixture is submitted to microwave treatment (150 Watts) during 15 min.

V-2) Synthesis of Polybutylphenothiazine XIV

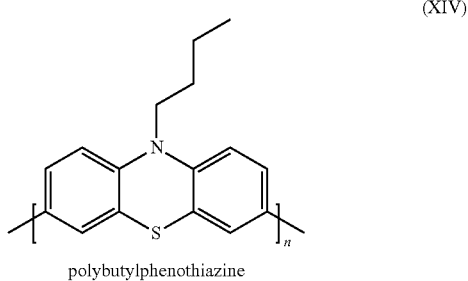

(XIV)

polybutylphenothiazine

Under inert atmosphere, Poly(I) (100 mg; 0.5 mmol) is added to a degassed DMSO solution (20 mL). The solution is heated for 1 day in order to let the polymer progressively solubilise in the solvent. Then, the solution is cooled to −80° C. before 1.1 molar equivalent of butyl-lithium (220 µL; 0.55 mmol) is added. The mixture is maintained under nitrogen atmosphere and stirring for 20 min at −80° C., then the stirring goes on for 2 hours without necessity of further cooling before the dropwise addition of 1.1 molar equivalent of 1-bromobutane (59 mL; 0.55 mmol). The solution is, after that, refluxed for 24 hours.

V-3) Synthesis of diphenothiazin-10H-yl ketone XV

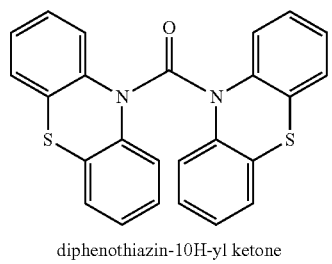

(XV)

diphenothiazin-10H-yl ketone

The synthesis of compound XV is based on a procedure described in S. Darvesh, R. S. McDonald, K. V. Darvesh, D. Mataija, S. Conrad, G. Gomez, R. Walsh, E. Martin/*Bioorganic and medicinal chemistry* 15, 2007, 6367-6378.

To compound I (1 g; 5 mmol) solution of dichloromethane (50 mL) is added one molar equivalent of triethylamine (700 µL; 5 mmol) and 5 molar equivalent of 10H-carbonylchloride-phenothiazine (6.677 g; 25 mmol). The solution is refluxed, stirred and checked by TLC analysis revealing the progressive consumption of I.

V-4) Synthesis of 10H-methylsulfonylphenothiazine XVI

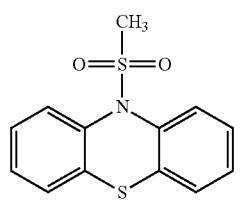

(XVI)

10H-methylsulfonylphenothiazine

The synthesis of compound XVI is based on a procedure described in J. J. Lafferty, E. Garvey, E. A. Nodiff, W. E. Thompson, C. L. Zirkle/*The Journal of Organic Chemistry* 27, 1962, 1346-1351.

A mixture of compound I (20 g; 100 mmol), 1.5 molar equivalent of methanesulfonyl chloride (17.2 g; 150 mmol), and 50 mL of pyridine is stirred at 27° C. for 24 hours.

V-5) Synthesis of 10H-methanesulfinylphenothiazine XVII

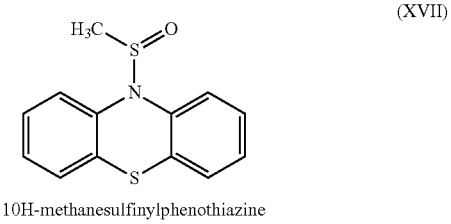 [SMILES: CS(=O)N1c2ccccc2Sc2ccccc21]

(XVII)

10H-methanesulfinylphenothiazine

The synthesis of compound XVII is based on a procedure described in A. M. Piggott, P. Karuso/*Tetrahedron letters* 48, 2007, 7452-7455. A solution of compound I (5.0 g; 25 mmol) in freshly dissolved dichloromethane (30 mL) is cooled to −80° C. under an atmosphere of nitrogen. A solution of 0.5 molar equivalent of methanesulfinyl chloride (1.205 g; 12.5 mmol) in freshly distilled dichloromethane (5 mL) is added dropwise, with vigorous stirring, over half an hour. The solution is then brought to room temperature over 2 h, and stirred at R.T for a further 1 h.

V-6) Synthesis of diphenothiazin-10H-yl-methylphosphite XVIII

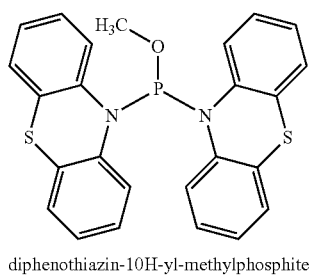

(XVIII)

diphenothiazin-10H-yl-methylphosphite

The synthesis of compound XVIII is based on a procedure described in P. A. Turhanen, R. Niemi, M. Peräkylä and T. Järvinen and J. J. Vepsäläinen/*Organic and biomolecular chemistry* 1, 2003, 3223-3226.

A mixture of PCl$_3$ (16 g; 120 mmol) in ether (100 mL) is cooled to 0° C. under a nitrogen atmosphere prior to the slowly addition of 1.08 molar equivalent of methanol (4.3 g; 130 mmol). The reaction mixture is allowed to warm to R.T with continuous stirring for 2 hours. Ether was first removed by distillation and the residue was further distilled to give MeOPCl$_2$ which was then dissolved in ether (200 mL) and treated with 4 molar equivalent of compound I and stirred for 48 hours at R.T.

V-7) Synthesis of 1-(diphenothiazin-10H-yl-phosphinyl)ethanone XIX

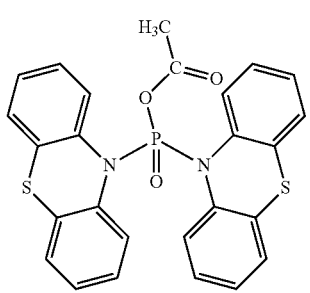

(XIX)

1-(diphenothiazin-10H-yl-phosphinyl)ethanone

XIX synthesis is carried out following procedure of preparative example V-6) (XVIII).

Compound XVIII (8.543 g; 17 mmol) is dissolved in ether (25 mL), and one molar equivalent of acetyl chloride (1.33 g; 17 mmol) is slowly added at 30° C. The reaction mixture is allowed to warm to R.T and the ether is removed in vacuo.

The invention claimed is:

1. A rechargeable metal or metal-ion cell comprising:
an anode comprising at least one metal;
a charge-carrying electrolyte comprising a charge carrying medium and at least one metal salt; and
an organic polymer cathode, wherein said cathode comprises at least one N-substituted polyphenothiazine polymer [polymer (P)], said polymer comprising at least one N-substituted phenothiazine recurring unit of formula:

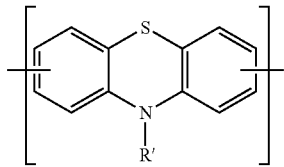

wherein R' is an electron-withdrawing group comprising at least one heteroatom selected from the group consisting of O, S, P, and N.

2. The cell of claim 1, wherein in the polymer (P), the R' group forms with the nitrogen atom of the phenothiazine ring at least one electron-withdrawing group selected from the group consisting of urethane group; urea group; thiourethane group; amide group; sulfonamide groups; sulfinamide group; hydrazine group; phosphonamide group; phosphinimide group; and phosphamide group.

3. The cell of claim 1, wherein the at least one N-substituted phenothiazine recurring unit of the polymer (P) is a unit having a formula selected from the group consisting of:

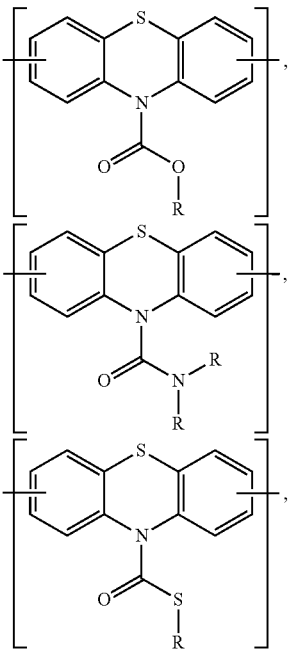

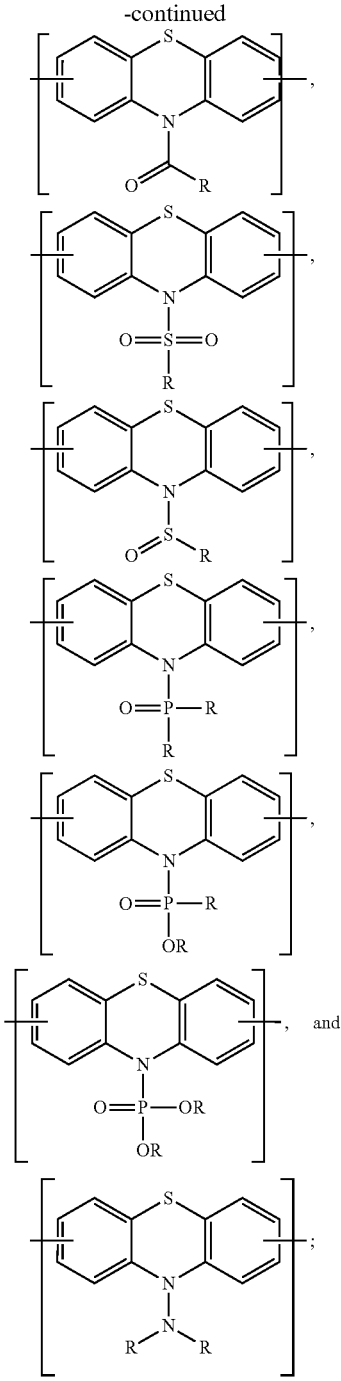

wherein each of R, equal to or different from each other and at each occurrence is H or a hydrocarbon group, optionally fluorinated, and optionally comprising one or more ionisable group.

4. The cell of claim 1, wherein the at least one N-substituted phenothiazine recurring unit further comprises at least one ionisable group selected from the group consisting of carboxylate groups, sulfonate groups, sulfonylimide groups, and phosphonate groups.

5. The cell according to claim 1, wherein said polymer (P) comprises recurring units selected from the group consisting of:

(I) urethane-containing phenothiazine recurring units of formula:

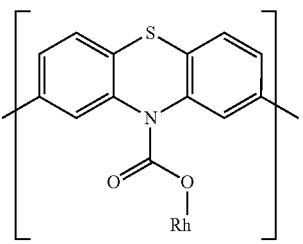

wherein Rh is a $C_1$-$C_{24}$ hydrocarbon group, optionally fluorinated, optionally comprising one or more heteroatoms comprised in an additional functional group; and (II) amide-containing phenothiazine recurring units of formula:

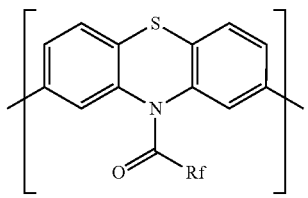

wherein Rf is a $C_1$-$C_{24}$ hydrocarbon group, optionally comprising one or more heteroatoms comprised in an additional functional group.

6. The cell according to claim 5, wherein said polymer (P) comprises recurring units of following formula (I-A) and/or recurring units of following formula (II-A):

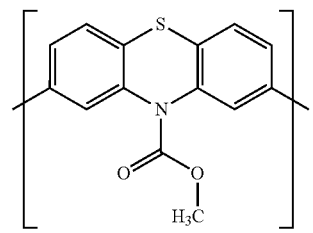
(I-A)

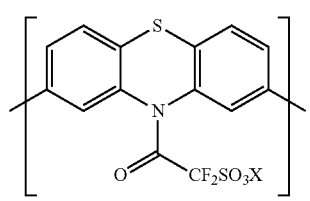
(II-A)

X in formula (II-A) being a metal.

7. The cell according to claim 1, wherein the metal ion cell is an alkaline or alkaline-earth secondary battery, wherein the anode comprises a negative electrodes material selected from the group consisting of:
alkaline or alkaline-earth metal;
graphitic carbons able to intercalate an alkaline or alkaline-earth metal;
alkaline or alkaline-earth metal alloy compositions; and
alkaline or alkaline-earth metal titanates, suitable for intercalating an alkaline or alkaline-earth metal with no induced strain.

8. The cell according to claim 7, wherein said alkaline or alkaline-earth secondary battery is a Lithium-ion cell wherein the anode comprises a negative electrodes material selected from the group consisting of:
graphitic carbons able to intercalate lithium;
lithium metal;
lithium alloy compositions;
lithium titanates;
lithium-silicon alloys; and
lithium-germanium alloys.

9. The cell according to claim 1, wherein said charge carrying medium is selected from the group consisting of ethylene carbonate, propylene carbonate, dimethyl carbonate, diethyl carbonate, ethyl-methyl carbonate, butylene carbonate, vinylene carbonate, fluoroethylene carbonate, fluoropropylene carbonate, gamma-butyrolactone, methyl difluoroacetate, ethyl difluoroacetate, dimethoxyethane, diglyme (bis (2-methoxyethyl)ether), non-protonic ionic liquids, poly (oxyethylene)s, and combinations thereof.

10. The cell according to claim 1, being a Lithium-ion cell; wherein said at least one metal salt is a lithium salt selected from the group consisting of $LiPF_6$; $LiBF_4$; $LiClO_4$; lithium bis(oxalato)borate; $LiN(CF_3SO_2)_2$; $LiN(C_2F_5SO_2)_2$; $M[N(CF_3SO_2)(R_FSO_2)]_n$ with $R_F$ being $C_2F_5$, $C_4F_9$, or $CF_3OCF_2CF_2$, and with M being Li; $LiAsF_6$; $LiC(CF_3SO_2)_3$; and combinations thereof.

11. A N-substituted polyphenothiazine polymer [polymer (P)], comprising at least one N-substituted phenothiazine recurring unit of formula:

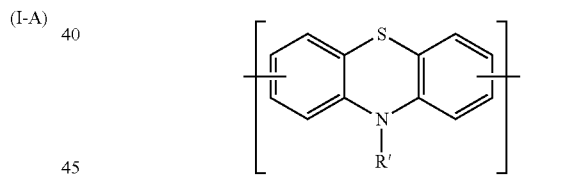

wherein R' is an electron-withdrawing group comprising at least one heteroatom selected from the group consisting of O, S, P, and N.

12. The N-substituted polyphenothiazine polymer according to claim 11, wherein the N-substituted phenothiazine recurring unit is a unit of formula selected from the group consisting of:

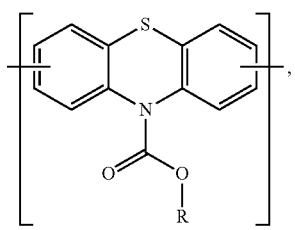

-continued

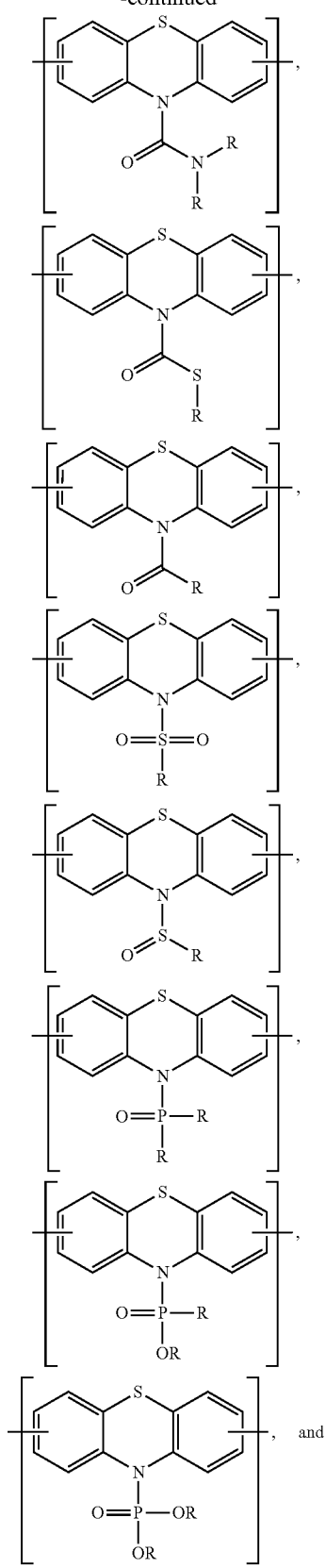

, and

-continued

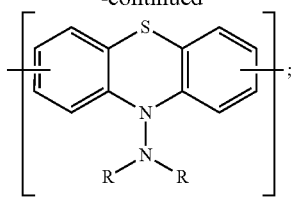

;

wherein each of R, equal to or different from each other and at each occurrence, is H or a hydrocarbon group, optionally fluorinated, and optionally comprising one or more ionisable groups.

13. The N-substituted polyphenothiazine polymer according to claim 11, wherein the N-substituted phenothiazine recurring unit further comprises at least one ionisable group selected from the group consisting of carboxylate groups, sulfonate groups, sulfonylimide groups, and phosphonate groups.

14. The N-substituted polyphenothiazine polymer according to claim 11, comprising recurring units of following formula (I-A) and/or recurring units of following formula (II-A):

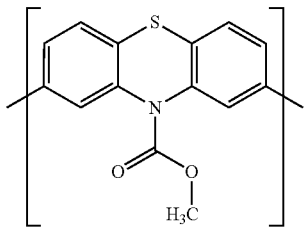 (I-A)

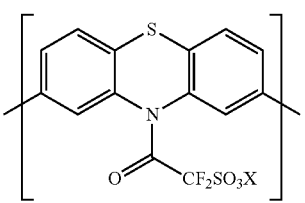 (II-A)

X in formula (II-A) being a metal.

15. The cell according to claim 1, wherein said polymer (P) only comprises recurring units derived from a N-substituted phenothiazine monomer.

16. The cell according to claim 1, wherein said polymer (P) is manufactured from N-substituted phenothiazine monomer derivatives having halogen group, borane groups, or other labile groups by coupling said N-substituted phenothiazine monomer derivatives.

17. The polymer according to claim 11, wherein said polymer (P) only comprises recurring units derived from a N-substituted phenothiazine monomer.

18. The polymer according to claim 11, which is manufactured from N-substituted phenothiazine monomer derivatives having halogen group, borane groups, or other labile groups by coupling said N-substituted phenothiazine monomer derivatives.

19. The polymer according to claim 11, wherein the N-substituted phenothiazine recurring unit further comprises at least one ionisable group selected from the group consisting of sulfonate groups and sulfonylimide groups.

* * * * *